US010799395B1

(12) United States Patent
Horner

(10) Patent No.: US 10,799,395 B1
(45) Date of Patent: Oct. 13, 2020

(54) TARSUS EYELID SUPPORT

(71) Applicant: Nathan Horner, Los Angeles, CA (US)

(72) Inventor: Nathan Horner, Los Angeles, CA (US)

( * ) Notice: Subject to any disclaimer, the term of this patent is extended or adjusted under 35 U.S.C. 154(b) by 419 days.

(21) Appl. No.: 15/970,570

(22) Filed: May 3, 2018

Related U.S. Application Data

(63) Continuation-in-part of application No. 14/868,326, filed on Sep. 28, 2015, now Pat. No. 10,076,448, which is a continuation-in-part of application No. 14/264,009, filed on Apr. 28, 2014, now abandoned, which is a continuation of application No. 14/042,736, filed on Nov. 6, 2013, now abandoned.

(51) Int. Cl.
*A61F 13/12* (2006.01)

(52) U.S. Cl.
CPC .................. *A61F 13/124* (2013.01)

(58) Field of Classification Search
CPC ............ A61F 9/04; A61F 13/124; A61F 2013/00497; A61F 2013/00502; A61F 9/007; A61F 13/0243; A61F 13/025
USPC ............... 128/858; 602/47, 52, 74
See application file for complete search history.

(56) References Cited

U.S. PATENT DOCUMENTS

| | | | |
|---|---|---|---|
| 2,527,947 A | 10/1950 | Loos | |
| 2,543,104 A * | 2/1951 | Golding | A61F 9/04 602/74 |
| 3,068,863 A | 12/1962 | Bowman | |
| 3,619,815 A * | 11/1971 | Towner, Jr. | A61F 9/04 2/12 |
| 4,134,401 A * | 1/1979 | Galician | A61F 9/00 602/74 |
| 4,727,869 A * | 3/1988 | Leonardi | A61F 13/124 602/74 |
| 4,867,146 A | 9/1989 | Krupnick et al. | |
| 4,979,811 A * | 12/1990 | Boyer | A61F 9/04 128/858 |
| 4,995,114 A * | 2/1991 | Price, Jr. | A61F 9/04 128/858 |

(Continued)

OTHER PUBLICATIONS

U.S. Appl. No. 14/264,009, now abandoned, filed Apr. 28, 2014, inventor/applicant Nathan Homer, and its prosecution history, including without limitation Office Actions, amendments, remarks, cited references, and any other potentially relevant documents. U.S. Appl. No. 14/264,009 is a parent application of the present application.

(Continued)

*Primary Examiner* — Kari K Rodriquez
(74) *Attorney, Agent, or Firm* — Kregg Koch

(57) ABSTRACT

Embodiments disclosed herein relate to a device and method for holding a superior tarsus of an eye in a closed position. Some embodiments of the device can comprise a first main surface configured to be applied against an upper eyelid having eyelashes when the upper eyelid is in a closed position such that an inferior edge of the eyelid patch is positioned above the eyelashes of the upper eyelid. The first main surface can have an adhesive thereon. The device is configured to be applied above the eyelashes, below the eyebrow, and to form multiple curvatures to maintain sufficient rigidity to maintain the upper eyelid in a closed position. Additionally, some embodiments of the device have thinned or more flexible portions that can improve the conformability and fit of the device to the user's anatomy.

17 Claims, 22 Drawing Sheets

(56) References Cited

U.S. PATENT DOCUMENTS

| | | | |
|---|---|---|---|
| 5,887,590 A | 3/1999 | Price | |
| 6,034,293 A | 3/2000 | Stamler | |
| 6,899,104 B1 | 5/2005 | Inman et al. | |
| RE39,896 E | 10/2007 | Arnold et al. | |
| 10,076,448 B2 | 9/2018 | Horner | |
| 2002/0100481 A1 | 8/2002 | Abbasi | |
| 2013/0172829 A1* | 7/2013 | Badawi | A61F 9/0017 604/294 |
| 2015/0122265 A1 | 5/2015 | Horner | |
| 2015/0150718 A1* | 6/2015 | Kuracina | A42C 5/02 2/181 |
| 2017/0112676 A1* | 4/2017 | Knepshield Williams | A61F 13/00085 |

OTHER PUBLICATIONS

3M Nexcare Flexible 1 inch Clear Tape, 20 YD Value Pack. Applicant submits that this product was in public use prior to the Applicant's filing date.

* cited by examiner

Thickness:
☐ .30 mm
☒ .25 mm

Lorem ipsum

Thickness:
☐ .30 mm
☒ .25 mm

Thickness:
☐ .30 mm
☐ .35 mm

TARSUS EYELID SUPPORT

CROSS REFERENCE TO RELATED APPLICATIONS

This application is a continuation-in-part of U.S. patent application Ser. No. 14/868,326, filed Sep. 28, 2015 (titled "Tarsus Eyelid Patch"), which is a continuation-in-part of U.S. patent application Ser. No. 14/264,009, filed Apr. 28, 2014 (titled "Artificial Perforated Tarsorrhaphy"), which is a continuation of U.S. patent application Ser. No. 14/042,736, filed Nov. 6, 2013 (titled "Artificial Perforated Tarsorrhaphy"). Each and all of the above-listed applications are hereby incorporated by reference as if fully set forth herein.

FIELD OF THE DISCLOSURE

Embodiments of the present disclosure relate to devices for aiding the healing of an eye surface or epithelium after injury or a medical procedure. More specifically, embodiments disclosed herein relate to devices for holding an eyelid in a closed position.

BACKGROUND

There has long been a clinical need for a device to hold an upper eyelid in a closed position for healing after various surgeries, injuries, or conditions. Tarsorrhaphy is a surgical procedure of sewing the eyelid closed. As illustrated in FIG. 1 (prior art), an upper eyelid is sewn together with the bottom eyelid to keep the eye closed during a healing period.

Other prior-art methods of holding the eyelid closed include the standard cloth eye patch, as shown in FIG. 2, and medical tape. Such conventional eye patches can smother the eye, can be uncomfortable, and can be inadequate for effectively keeping the eyelid in a closed position. Therefore, eye doctors commonly use a Tarsorrhaphy as the standard method of keeping the eyelid closed. Still other methods for holding an eyelid closed for eye healing include substantially rigid eye splints, such as is disclosed in U.S. Pat. No. 6,034,293 to John F. Stamler. The rigid eye splint has proven to be uncomfortable for the user wearing the device.

Accordingly, there is a need for a device that painlessly and comfortably holds an upper eyelid in a closed position, thereby keeping the eye closed and allowing the eyelid to be the eye's natural bandage and permitting defects on an eye's surface to heal.

BRIEF SUMMARY OF THE DISCLOSURE

Embodiments disclosed herein relate to an improved eyelid support (also referred to herein as a patch, cover, brace, or splint) for keeping an upper eyelid in a closed position for an extended period of time. Keeping the eye in a closed position can allow defects on the eye surface to heal properly and, importantly, can do so comfortably with a lower amount of trauma to the eyelid as compared to the surgical procedure of tarsorrhaphy, which entails suturing the upper and lower eyelids together.

In any embodiments disclosed herein, the eyelid support can have a main body having a medial edge, a lateral edge, a superior edge, and an inferior edge. The main body can have a first surface and a second surface, the second surface opposing the first surface. Any embodiments of the eyelid support can have an adhesive on the first surface. The adhesive can be biocompatible, and can be used to adhere the eyelid support to an outside surface of an upper eyelid. In any embodiments of the eyelid support, the main body can be comprised of a perforated mesh material that is non-rigid. Embodiments of the tarsus support disclosed herein utilize and represent the latest advancements in medical materials and adhesives, as well as scientific and ophthalmological technologies and innovations.

In any embodiments, the first surface of the main body can be configured to be positioned against an upper eyelid in a position wherein the superior edge of the main body of the eyelid support is positioned below an eyebrow. In any embodiments disclosed herein, the main body of the eyelid support can be positioned over all or a portion of the user's eyebrow so that a top portion of the eyelid support extends over the user's brow. The main body of the eyelid support can be pressed and conformed against the skin covering the superior tarsus when the superior tarsus is in a closed position, thereby forming a convex curve in the main body of the eyelid support in the region of the eyelid support that is adjacent to the superior tarsus. Any embodiments can further be configured to attach to and conform to the skin covering the superior tarsus when the superior tarsus is in the closed position, thereby forming a concave curve over the superior tarsus. Additionally, a convex curve can be formed in the nonrigid eyelid support in the region adjacent to the concave portion, in other words, adjacent to the skin covering the superior tarsus. As so configured, when the non-rigid device forms the concave curve and the convex curve when the superior tarsus is in the closed position, the combination of the concave and convex curvatures can add significant strength and stiffness to the eyelid support to hold the superior tarsus in the closed position.

In any embodiments disclosed herein, the eyelid support can further have a medial edge and a lateral edge sized and configured to expose a medial and lateral canthus of the eye, respectively, when the main body of the device is coupled with the skin covering the superior tarsus, when the superior tarsus is in the closed position. In this arrangement, the device can allow a medication to be inserted into the exposed medial and lateral canthus of the eye when the main body of the eyelid support is coupled with the skin covering the superior tarsus, when the superior tarsus is in the closed position.

In any embodiments disclosed herein, the eyelid support can be formed from a single layer, or two or more layers of perforated or vapor permeable material. The material can be selected from any suitable material that is biocompatible, including, without limitation, at least one of or combination of a mesh fabric material, a hypoallergenic plastic material, and a medical tape material (latex free, or otherwise).

Embodiments disclosed herein also relate to a method for holding a superior tarsus of an eye in a closed position, comprising the steps of applying a tarsus eyelid support to the skin covering the superior tarsus, conforming the eyelid support to the skin in the region above the superior tarsus and below an eyebrow when the superior tarsus is in the closed position, thereby forming a concave curve over the skin covering the superior tarsus in combination with a convex curve in the portion of the eyelid support adjacent to the skin covering the superior tarsus. In any embodiments, the method for holding a superior tarsus in the closed position can also comprise adhering the eyelid support to the skin covering the superior tarsus above the eyelashes, when the superior tarsus is in the closed position. The method can also comprise exposing a medial and lateral canthus of the eye when the superior tarsus is in the closed position, thereby allowing a medication to be applied or inserted into the medial and lateral canthus of the eye when the superior tarsus is in the closed position. When the superior tarsus is in the closed position, the eyelid support tarsus eyelid patch can be formed against the skin covering the superior tarsus so as to form a concave curve in a horizontal and a vertical direction in the region covering the superior tarsus. Additionally, the eyelid support can be formed against the skin around (above, but below the eyebrow, and to the sides of) the superior tarsus, to form a convex curve in the tarsus eyelid support around the concave portion attached to the skin covering the superior tarsus. The combination of the convex and concave curves creates the stiffness of the tarsus eyelid support and enables the ability of the eyelid support to hold the eyelid in the closed position.

Some embodiments are directed to a support device for holding a superior tarsus of an eye in a closed position, comprising a main body having a first main surface, a second main surface, a first lateral edge, a second lateral edge, a top edge, and a bottom edge, adhesive coupled with the second main surface, the second main surface being the surface that is positionable against a user's upper eyelid when the support device is in an operable position, and a first flex zone formed in the main body of the support device. The flex zone can have a bend stiffness that is lower than a bend stiffness of the portions of the main body adjacent to the flex zone. The support device can be sized and configured to be positioned above a user's upper eyelash and below a user's eyebrow. The support device can be configured to be conformed against a skin surface of the user above the user's upper eyelid when the user's upper eyelid is in a close position. The support device can be configured to hold the user's upper eyelid in a closed position. The first flex zone if configured to improve the conformability of the support device to the user's anatomy.

Some embodiments are directed to a support member for holding a user's upper eyelid in a closed position, comprising a main body having a first main surface, a second main surface, a first lateral edge, a second lateral edge, a top edge, and a bottom edge. The second main surface can be coated in adhesive, the second main surface being the surface that is positionable against a user's upper eyelid when the support member is in an operable position. The support member can have a first stiffened zone formed in the main body of the support member; and a first flex zone formed in the main body of the support member. The support member can be configured to be conformed against a skin surface of the user above the user's upper eyelid when the user's upper eyelid is in a close position. The support member can be sized and configured such that the bottom edge is positioned above the user's upper eyelash when the support member is in an operable position on the user. The support member can be sized and configured such that the top edge is positioned on the user's brow when the support member is in an operable position on the user. The support member can be configured to hold the user's upper eyelid in a closed position when the support member is in an operable position on the user. The first stiffened zone can have a thickness that is significantly greater than a thickness of the first flex zone. The first stiffened zone can be sized and positioned on the main body to generally cover the user's upper eyelid when the support member is in an operable position on the user. The first flex zone positioned above and to the sides of the first stiffened zone to increase the flexibility of the main body in the main body adjacent to the first stiffened zone.

DETAILED DESCRIPTION OF SOME EXEMPLIFYING EMBODIMENTS

Figure 1:
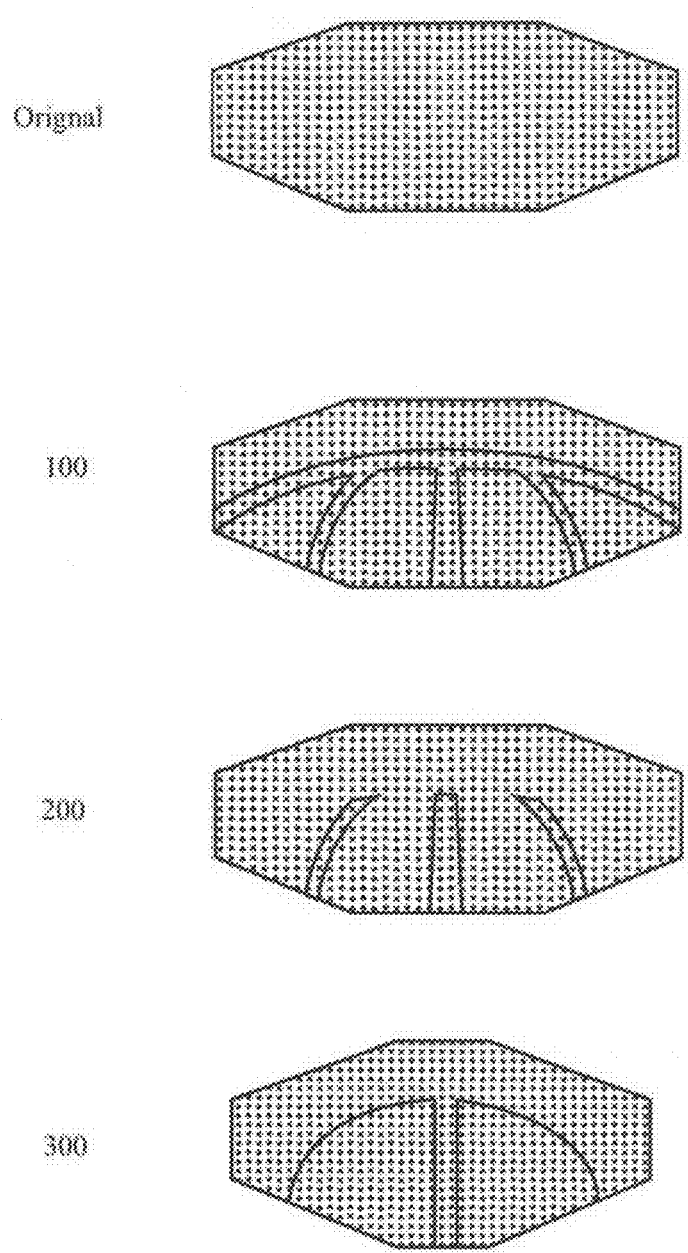
FIG. 1 shows the top views of four different support support embodiments.

Embodiments of systems, components and methods of assembly and manufacture will now be described with reference to the accompanying figures, wherein like numerals refer to like or similar elements throughout. Although several embodiments, examples, and illustrations are disclosed below, it will be understood by those of ordinary skill in the art that the inventions described herein extend beyond the specifically disclosed embodiments, examples, and illustrations and can include other uses of the inventions and obvious modifications and equivalents thereof, and combinations of any of the embodiments, features, and details of any of the embodiments disclosed herein with other of the embodiments disclosed herein. Additionally, it should be noted that the descriptions of all of the embodiments disclosed herein should be interpreted to include any of the features, components, and other details of any of the other embodiments disclosed here in combination with or in the alternative to any of the features, components, and other details explicitly described herein.

Additionally, the terminology used herein is not intended to be interpreted in any limited or restrictive manner simply because it is being used in conjunction with a detailed description of certain specific embodiments of the inventions. Also, embodiments of the inventions can comprise several novel features and no single feature is solely responsible for its desirable attributes or is essential to practicing the inventions herein described.

Certain terms may be used in the following description for the purpose of reference only, and thus are not intended to be limiting. For example, terms such as "above" and "below" may refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

User comfort is an important attribute of at least some embodiments of the tarsus eyelid cover. Having undergone multiple eye surgeries, and continuing to undergo eye surgeries, the inventor of the embodiments disclosed herein is continually experimenting with new designs, ideas, and alternative solutions for keeping his eyelid in the closed position following the surgery, through the creation and trial of various functional prototypes on his own upper eyelid, the inventor has developed the innovative and improved designs disclosed in this application. Such improved designs can improve the comfort, fit and therefore the function of the device. These innovated prototypes can be manufactured with more precision and accuracy, addressing and improving all aspects of the Tarsus Eyelid Patch and its functions.

Comfort is very important to long-term use of some of the embodiments of the eyelid support embodiments disclosed herein. In some cases, an eyelid support must be worn on a daily basis for many weeks, holding the eyelid down, thereby keeping the eye closed to heal the eye. Embodiments disclosed herein can be used to treat severe or chronic surface defects or issues of the eye, as in the case of the inventor of the embodiments disclosed herein. At least some of the embodiments disclosed herein are configured to provide a more secure, consistent, and comfortable eyelid support for the user. Some embodiments of the eyelid supports disclosed herein have been designed to have two or more different thicknesses about the main body of the eyelid cover. Certain portions of the main body can have a reduced or lesser thickness to make such sections more flexible than other portions of the cover. This can result in improved conformability of the eyelid support to the anatomy of the user, increasing user comfort and effectiveness of the eyelid cover.

In some embodiments, the thicknesses of the eyelid support is very important to the comfort, performance, and effectiveness of the eyelid support when applied to the upper eyelid and the curvatures of the eyeball and the orbital eye socket. The mesh or perforated material used in some embodiments of the eyelid support can be made to be thick enough to become rigid when curved, yet flexible enough to conform to the curvatures of the orbital eye socket. If the material is too thin, in some embodiments, the eyelid support can become too flimsy to perform the important hyperbolic paraboloid functions. Yet precise slight thinning, or increased thickening in designated areas or patterns can significantly improve the ability of the eyelid support to form optimal bends, creases, or curves at the desired locations to best conform to the anatomy of the eye socket of the user, and provide sufficient stiffness to the eyelid support to maintain the eyelid in the closed position without compromising the stiffness of the device.

Figure 1A:
FIG. 1A shows a front view photograph of actual Tarsorrhaphy procedure where the eyelids are sewn closed.
Figure 2:
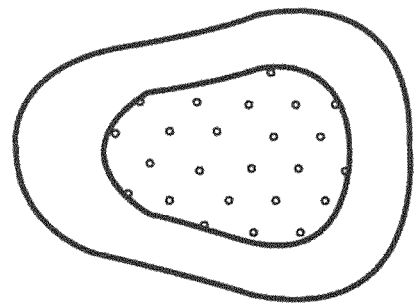
FIG. 2 shows a conventional eye patch.
Figure 1B:
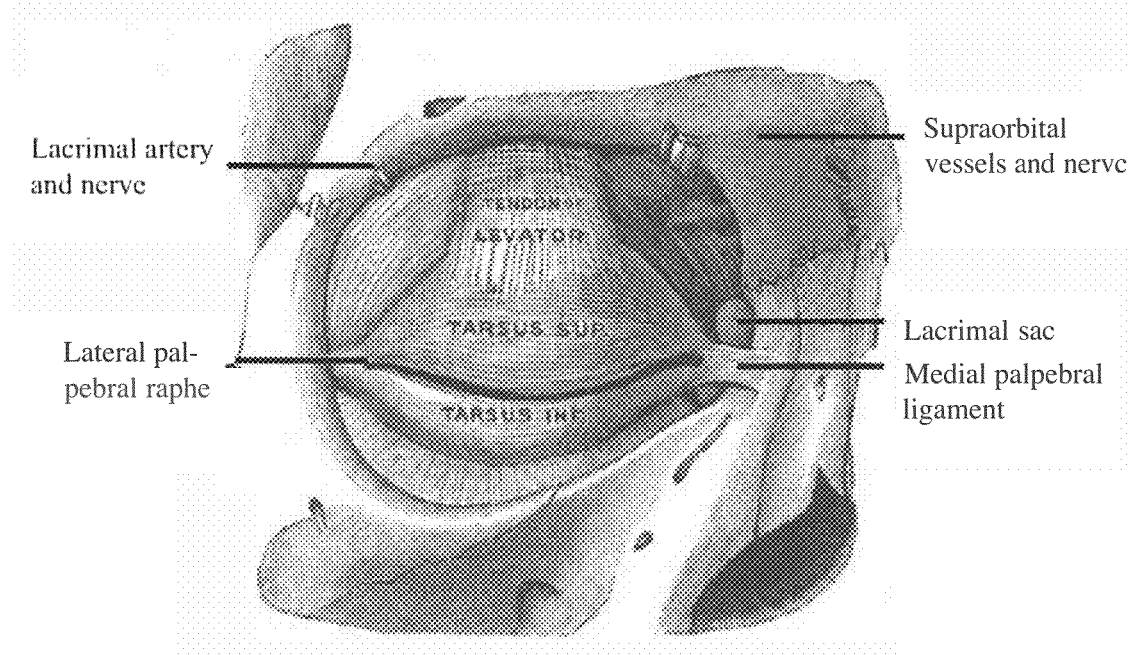
FIG. 1B shows the anatomy of an eye socket.

Embodiments of the eyelid support disclosed herein are designed and configured to keep the eyelid in a closed position to heal defects on an eye's surface, as a painless option to Tarsorrhaphy, which is a standard surgical procedure of sewing the eyelids closed. Tarsorrhaphy is illustrated in FIG. 1A (prior art). In the anatomy of the eye, as shown in FIG. 1B, the tarsus is a thin sheet of fibrous connective tissue that supports the edge of each eyelid. The eyelids protect and help lubricate the eyes. The eyelid skin itself is very thin, containing no subcutaneous fat, and is supported by a tarsal plate. This tarsal plate is a fibrous layer that gives the lids shape, strength, and a place for muscles to attach. The tarsi or tarsal plates are two comparatively thick, elongated plates of dense connective tissue, about 2.5 cm (1.0 in) in length, one is found in each eyelid and contributes to its form and support. They directly abut the lid margins. The tarsus has a lower and upper part making up the palpebrae. The superior tarsus, tarsus superior or superior tarsal plate, the larger, is of a semilunar form, about 10 mm (0.4 in) in breadth at the center, and gradually narrowing toward its extremities. It is adjoined by the superior tarsal muscle to the anterior surface of this plate the aponeurosis of the levator palpebrae superioris is attached. The inferior tarsus, tarsus inferior or inferior tarsal plate, is smaller than the superior tarsus. It is thin, and elliptical in form, and has a vertical diameter of about 5 mm (0.2 in). The free or ciliary margins of these plates are thick and straight. The angle formed by the meeting of the upper and lower eyelids or superior tarsus and inferior tarsus, at either side of the eye is defined as the canthus. The medial canthus is the corner formed near the nose bridge. The lateral canthus is the corner formed distal the nose bridge.

Embodiments of the eyelid support of the present disclosure relate to improved procedures and devices for medically treating an eye after various surgeries or injuries, and for maintaining the health of the eye in the case of many other eye issues. Such embodiments can also be used to hold the eye in a closed position during nighttime hours or when the user is at rest or sleeping and can be particularly useful for users who suffer from dry eye, lazy eye, and strokes. It will be appreciated by those in the art that embodiments of the eyelid support disclosed herein can be used by anesthesiologists during non-eye related surgeries and medical procedures where anesthesia renders a patient unconscious and a need arises to keep the anesthetized patient's eyes closed.

Figure 3:
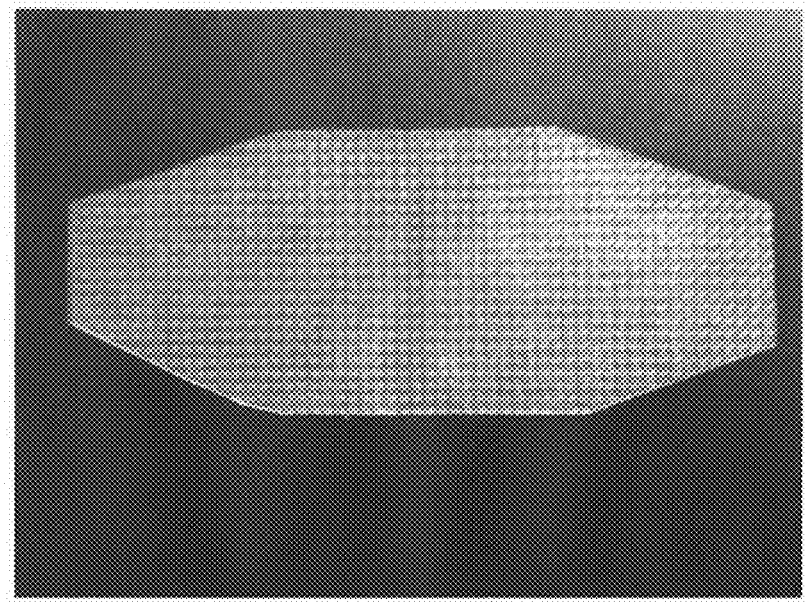
FIG. 3 is a photograph showing a top view of an embodiment of an improved eyelid support of the present disclosure.
Figure 4:
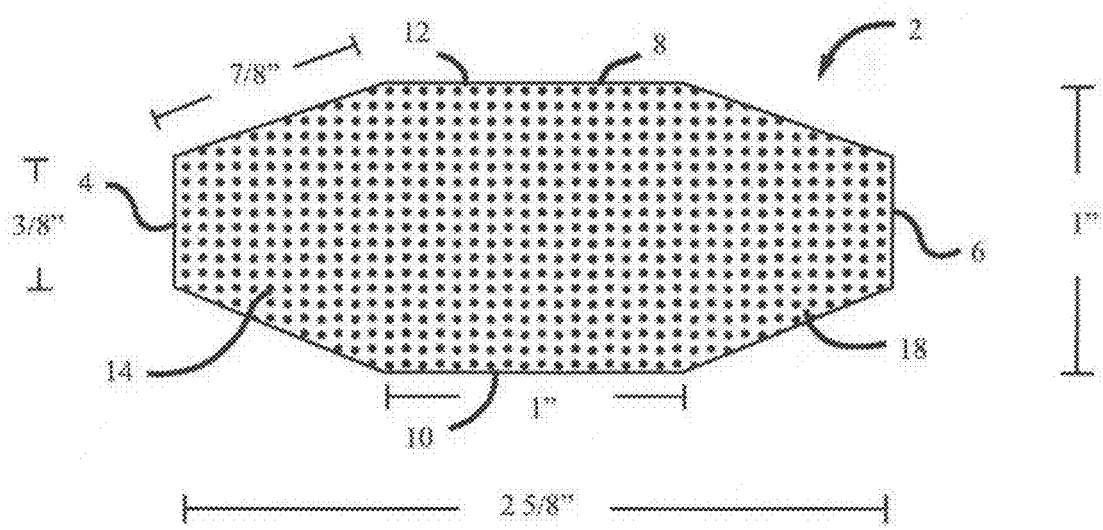
FIG. 4 is a top view of an embodiment of an improved eyelid cover, with exemplifying, nonlimiting measurements that can be applied to any embodiments disclosed herein.
Figure 5:
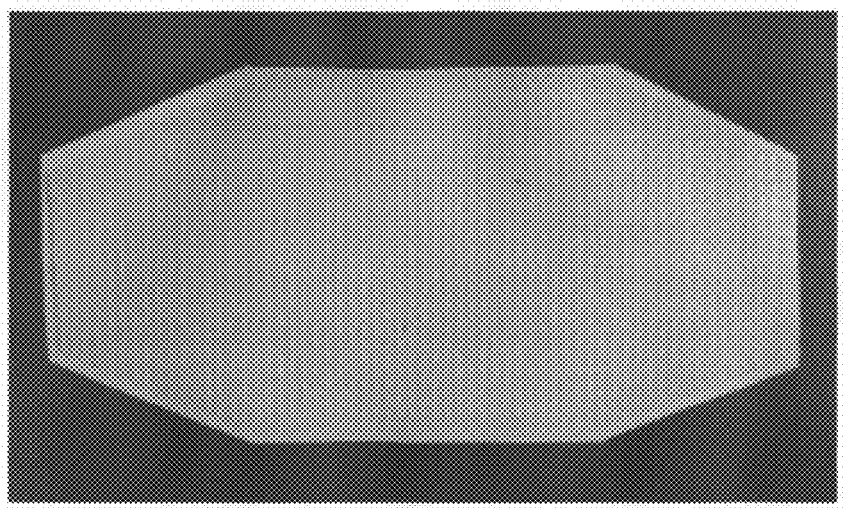
FIG. 5 is a photograph showing a top view of an embodiment of an improved eyelid support of the present disclosure.
Figure 6:
FIG. 6 is a front view photograph of the embodiment of the improved eyelid support shown in FIG. 4.

As illustrated in the accompanying figures, any embodiments disclosed herein can be made from a perforated mesh material. FIGS. 3 and 5 are photographs of two embodiments of the eyelid support that were made from perforated mesh material. FIG. 5 is a drawing of another embodiment of an eyelid support device 2. As illustrated, the eyelid support 2 can have a first lateral edge 4 that support can be inserted into or adjacent to an eye socket 22 medial canthus 24 of a user's face. A lateral edge 6, or distal edge, of the eyelid support 2 can be opposite the medial edge 4. In any embodiments, the eyelid support can further have an adhesive surface 12 (referenced to but not shown), a non-adhesive surface 14, an superior edge 8, and an inferior edge 10.

Figure 7:
FIG. 7 is a photograph showing a side view of an embodiment of the improved eyelid support of FIG. 4 applied to an upper eyelid and brow of a user.
Figure 8:
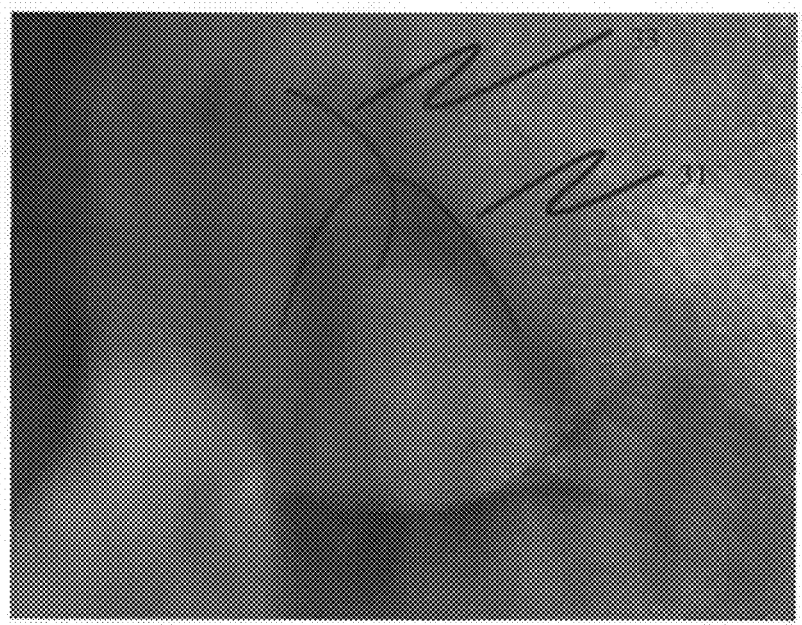
FIG. 8 is a close-up photograph of the embodiment of the improved eyelid support shown in FIG. 4, showing how the eyelid support device conforms to the eye socket and under brow, and (optionally) leaves the corners of the eyes exposed.
Figure 9:
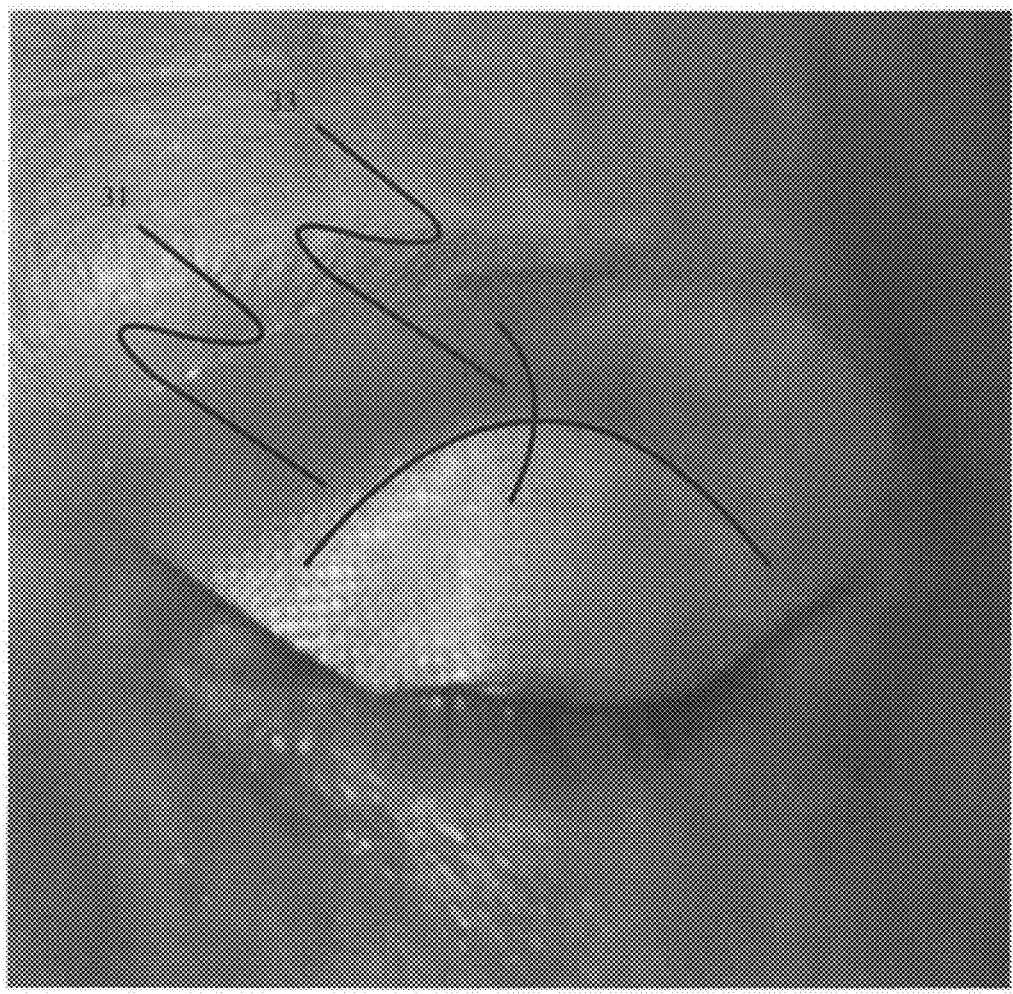
FIG. 9 is a close-up front view photograph of the embodiment of the improved eyelid support shown in FIG. 4.
Figure 10:
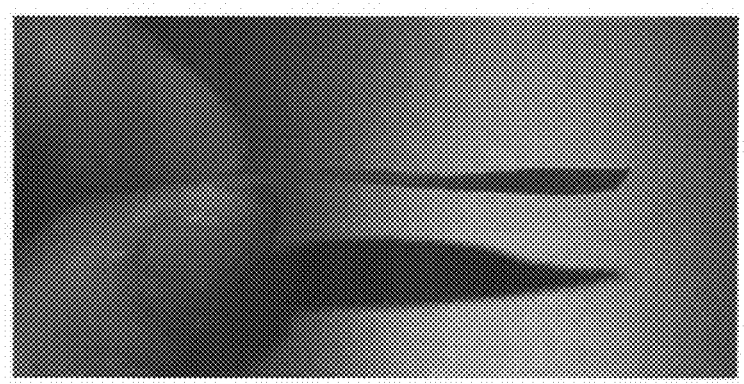
FIG. 10 is a photograph showing a side view or thickness of the embodiment of the improved eyelid support of FIG. 5.
Figure 11:
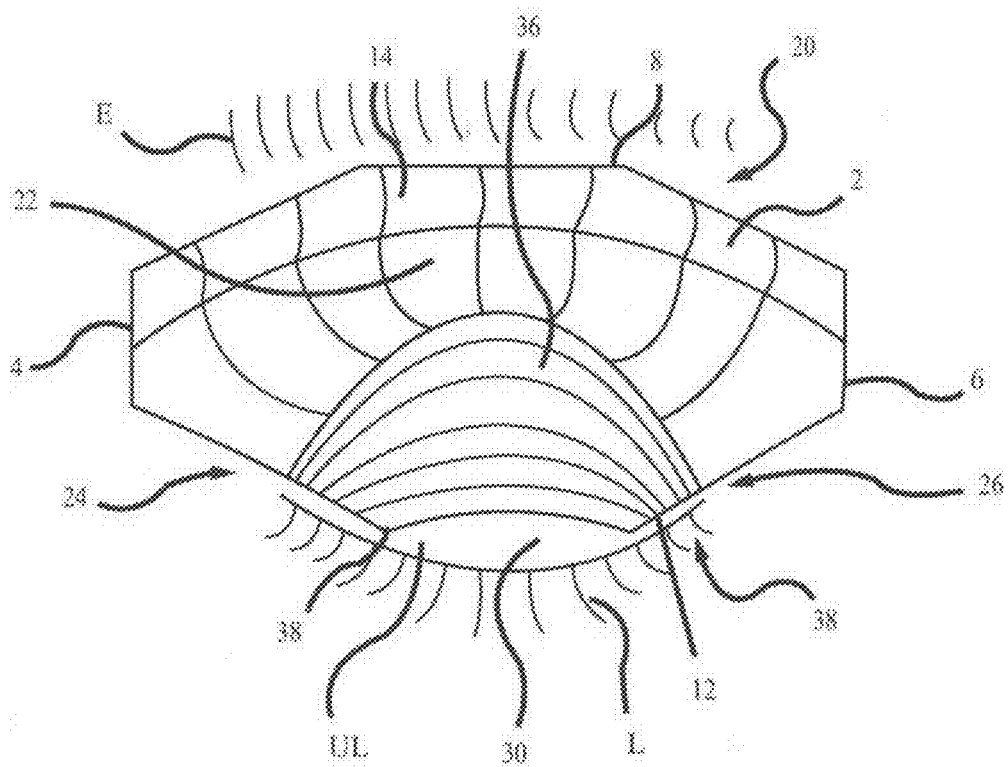
FIG. 11 is an enlarged view of the embodiment of the improved eyelid support shown in FIG. 4, applied to an upper eyelid and brow of a user.
Figure 12:
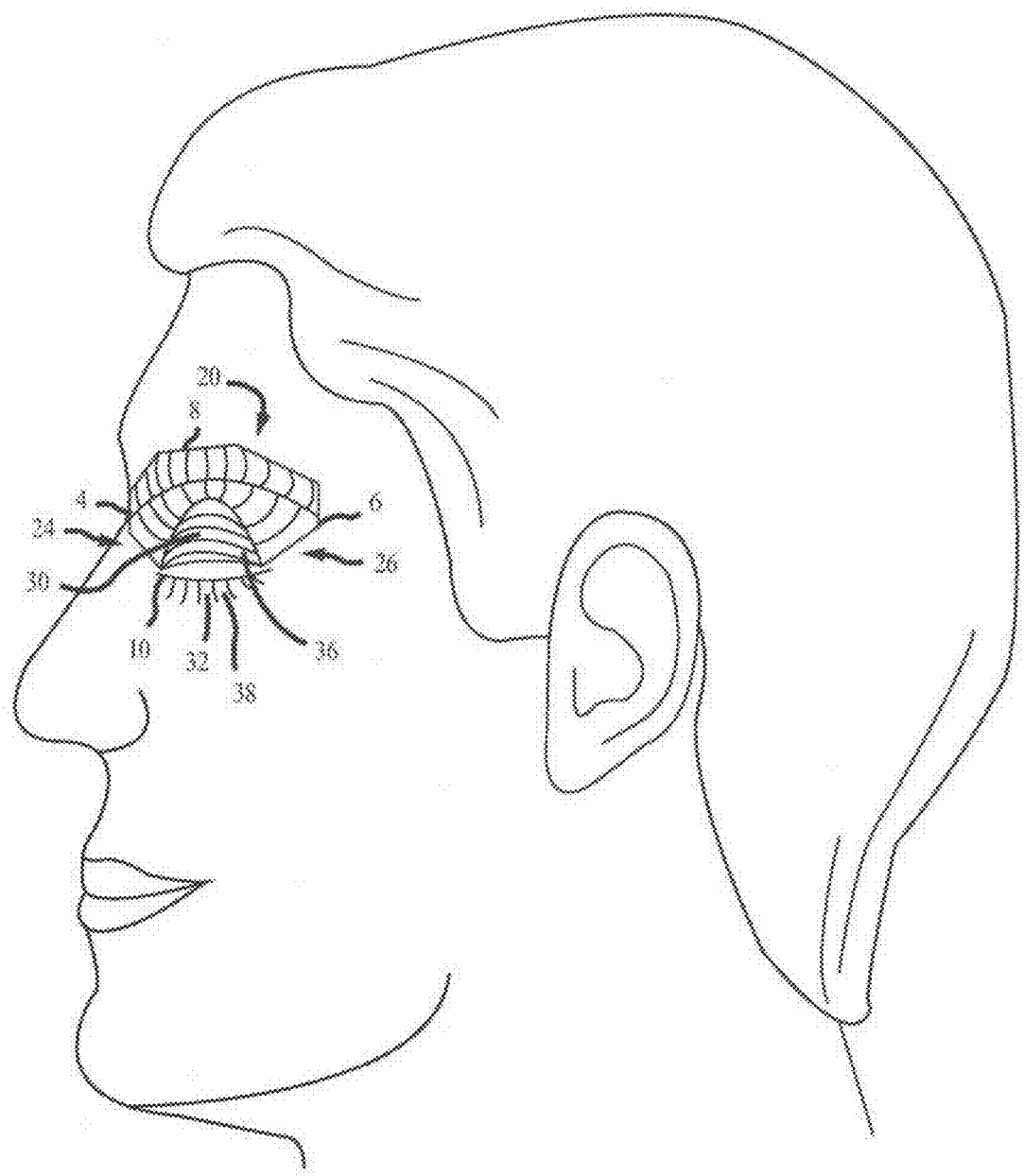
FIG. 12 is a side view of the embodiment of the improved eyelid support shown in FIG. 4, applied to an upper eyelid and brow of a user.
Figure 13:
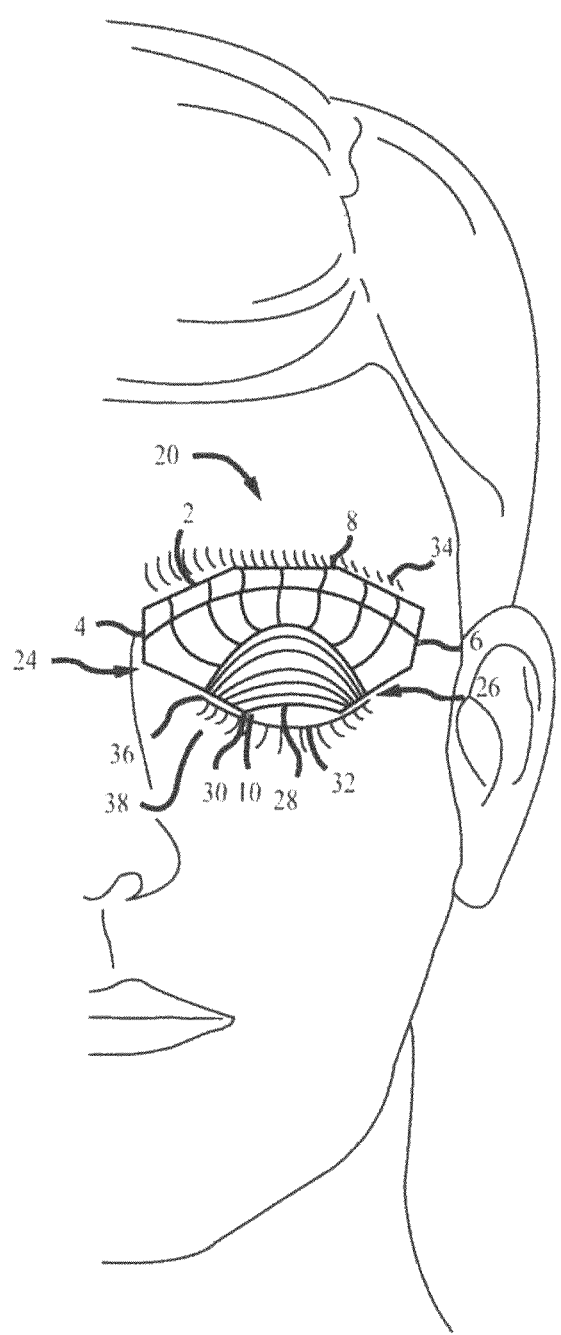
FIG. 13 is a front view of the embodiment of the improved eyelid support shown in FIG. 4, applied to an upper eyelid and brow of a user.
Figure 14:
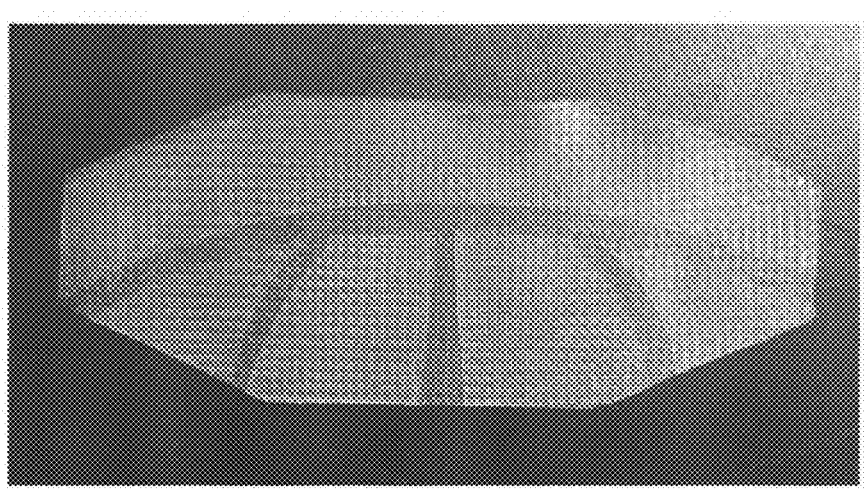
FIG. 14 is a photograph of a top view of another embodiment of an eyelid support.

As illustrated in FIGS. 7-9, the superior edge 8 of the eyelid support 2 can be inserted onto the eye socket 22 below the eyebrow 34 and the eyelid support bottom/inferior edge 10 can be applied onto the skin of the user's upper eyelid 30 above the inferior tarsus 32, pressing the eyelid support 2 against the skin to cause the eyelid support to conform to the anatomy of the eye socket. The eyelid support adhesive surface 12 can be adherable to the skin of the user's upper eyelid and the skin on the brow of the user (which can be, though is not required to be) below the eyebrow of the user. The eyelid support can be configured such that the non-adhesive surface 14 of the eyelid support does not contact the eye socket 22 nor the superior tarsus 30.

In the accompanying photographs and drawings, the eyelid support 2 can be positioned on the user's left eye with medial edge 4 (also referred to herein as a nose corner edge 4) being placed on the left side of the user's face. However, it should be appreciated that the device is interchangeable for use on both the left and right sides of the user's face. When using the eyelid support on the right eye, either the same device as illustrated or a symmetrical devices relative to the device illustrated can be used. In some embodiments, the reference numerals 4 and 6 may be interchanged to depict that the medial edge/nose corner edge 4 of the present device is inserted onto the user's right facial area.

As shown in FIG. 9, when the eyelid support is conformed to the user's eyelid, eye socket, the eyelid support can become concave in a first region (the region of the eyelid support that conforms to the edge of the eye socket) and convex in a second region (the region that covers the eyelid over the eyeball). In this configuration, the concave curvature in the first region and/or the convex curvature over the eyelid stiffens the eyelid support to provide a rigid support to the eyelid support that maintains the eyelid in a closed position. The curvatures make the otherwise flexible device act like the corrugation in steal, adding strength to the device, while achieving its function to hold the eyelid in a closed position. Depending on the size of the eyelid support 2, in some embodiments, the eyelid support 2 upper material can be conformed around the under brow (preferably, but not required to be, under a user's eyebrow E). The eyelid support 2 lower material assume the contour shape of the eye ball 36, holding the superior tarsus 30 in the closed position.

It is well known that adding curvature to a flexible surface adds strength and rigidity. Notable examples are making stiff cardboard from paper and Pringles® potato chips stored in cans. Here, the tarsus eyelid patch achieves curves when affixed to the region of the eye sockets below the eyebrow and to the closed eyelid. When affixed, the tarsus eyelid patch is concave in the horizontal direction in the region between the eyebrow and the upper eyelid, and the eyelid tarsus patch is convex in the vertical direction over the closed superior tarsus.

In some embodiments, the union of a convex and a concave curves can form a hyperbolic paraboloid curve whose general equation in Cartesian coordinates is:

$$\frac{z}{c} = \frac{y^2}{b^2} - \frac{x^2}{a^2}$$

A hyperbolic paraboloid surface gains strength and rigidity by balancing the compressive forces of the convex region with the tensile forces of the concave region. A hyperbolic paraboloid surface is characterized by having vertical parabolic cross sections and horizontal hyperbolic cross sections.

In any embodiments, the eyelid support 2 may be made of two 1-ply material sheets of medical tape. In any embodiments, the eyelid support 2 may be made of one single ply of a thicker adhesive backed material. The material can be hypoallergenic, suitable for medical applications, latex-free and/or perforated. The material can be opaque or transparent. Common medical tape material can be used for any of the embodiments of the eyelid support disclosed herein, including, but not limited to, 3M™ TRANSPORE™ tape.

In any embodiments, the eyelid support can be molded or formed as a single piece. The eyelid support can also be made out of other suitable perforated or non-perforated adhesive medical material(s). Having perforated or porous material can permit the skin under the eyelid support to breathe and emit moisture, increasing the comfort of the support. For example, any embodiments can be made from a 2-ply medical material of at least one of a mesh fabric material, a hypoallergenic plastic material, or a latex free tape material, all having an adhesive surface and optionally being made from a porous or perforated material.

As shown in the Figures, the eyelid support 2 can have angled or chamfered corners so as to permit access to or exposure of the corners of the eyes, which can improve comfort, and can also permit access for adding medicine into the corners of the eyes when the eyelid is closed. As illustrated in the FIGS. 3, 5, 9, 14, 18, 20, and 24, any embodiments of the support can be made from a vapor transmissible material (which can be a perforated or mesh material) that can permit the user's skin under the support to breathe.

In any embodiments, the eyelid support 2 dimensions can be approximately 2⅝ inch in length×approximately 1 inch in height×approximately 0.0135 inch thickness. Metric measurements may be approximately 5.7 cm length×approximately 2.5 cm height×approximately 30 mm thickness. However, it should be appreciated that the measurements and dimensions can be modified to and/or preformed at different dimensions to better suit a specific user's facial features. In any embodiments, the support can be made from a material that can be easily cut or otherwise modified in size, as needed. Further, any embodiments can be made from an adhesive that can hold the support firmly against the skin, while still being easily removable without damage or trauma to the skin.

In any embodiments, such as the support embodiment shown in FIG. 8, the eyelid support can be applied to support the user's upper eyelid in a closed position by first centering the eyelid support over the user's closed upper eyelid. The user can then align the inferior edge 10 of the support 2 just above the center of the opening of the eye on the upper eye lid above the eyelash L, and can then gently conform the support 2 onto the skin of the upper eyelid, around the radius of the eye ball, and up into the socket to form the multiplicity of concave and convex curvatures that result in sufficient stiffness to support the eyelid in the closed position. In any embodiments, the support 2 can also be applied to cover the under part of the eyebrow 34, adhering the device 2 to the superior tarsus 30. Applying the support in this manner can hold the superior tarsus in the closed position, thereby keeping the eye closed.

Figure 15:
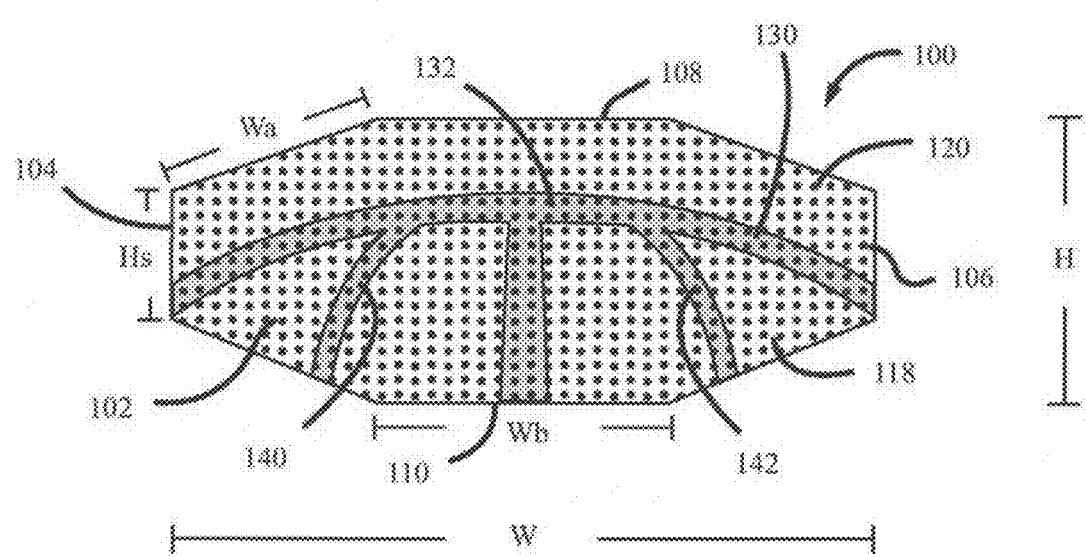
FIG. 15 is a top view of another embodiment of an improved eyelid support with exemplifying, nonlimiting measurements.
Figure 16:
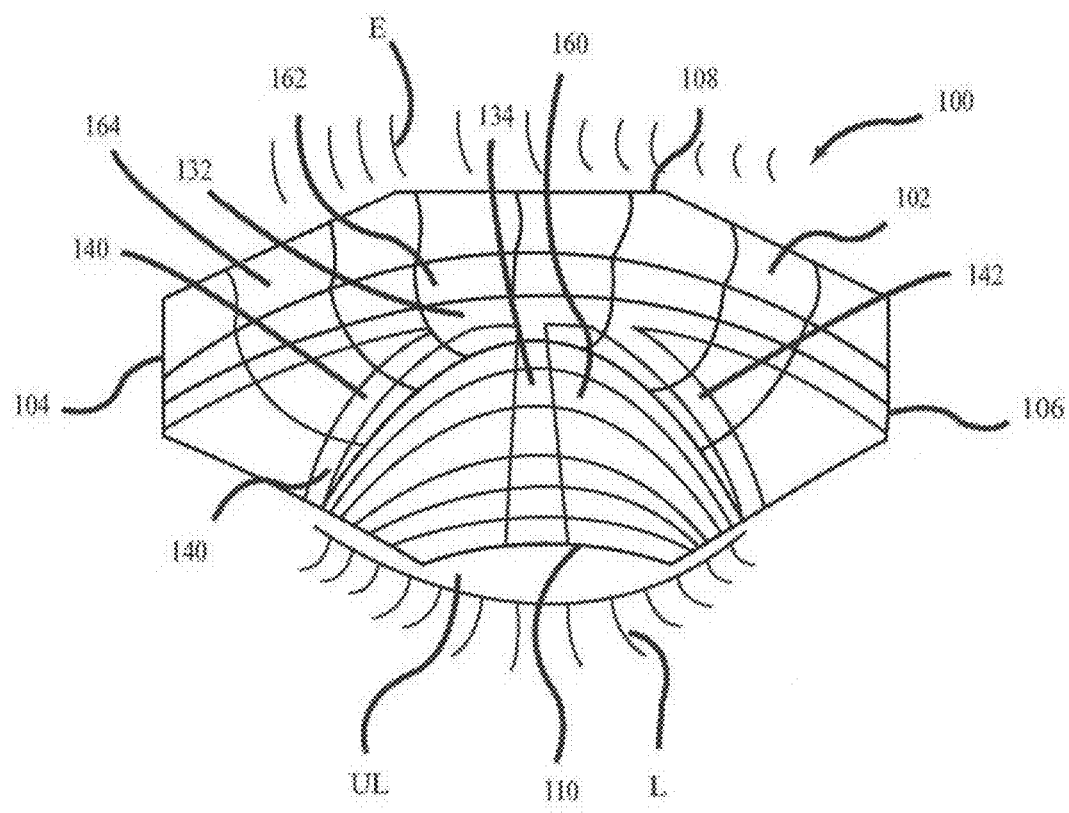
FIG. 16 is an enlarged view of the embodiment of the improved eyelid support shown in FIG. 14, applied to an upper eyelid and brow of a user.
Figure 17:
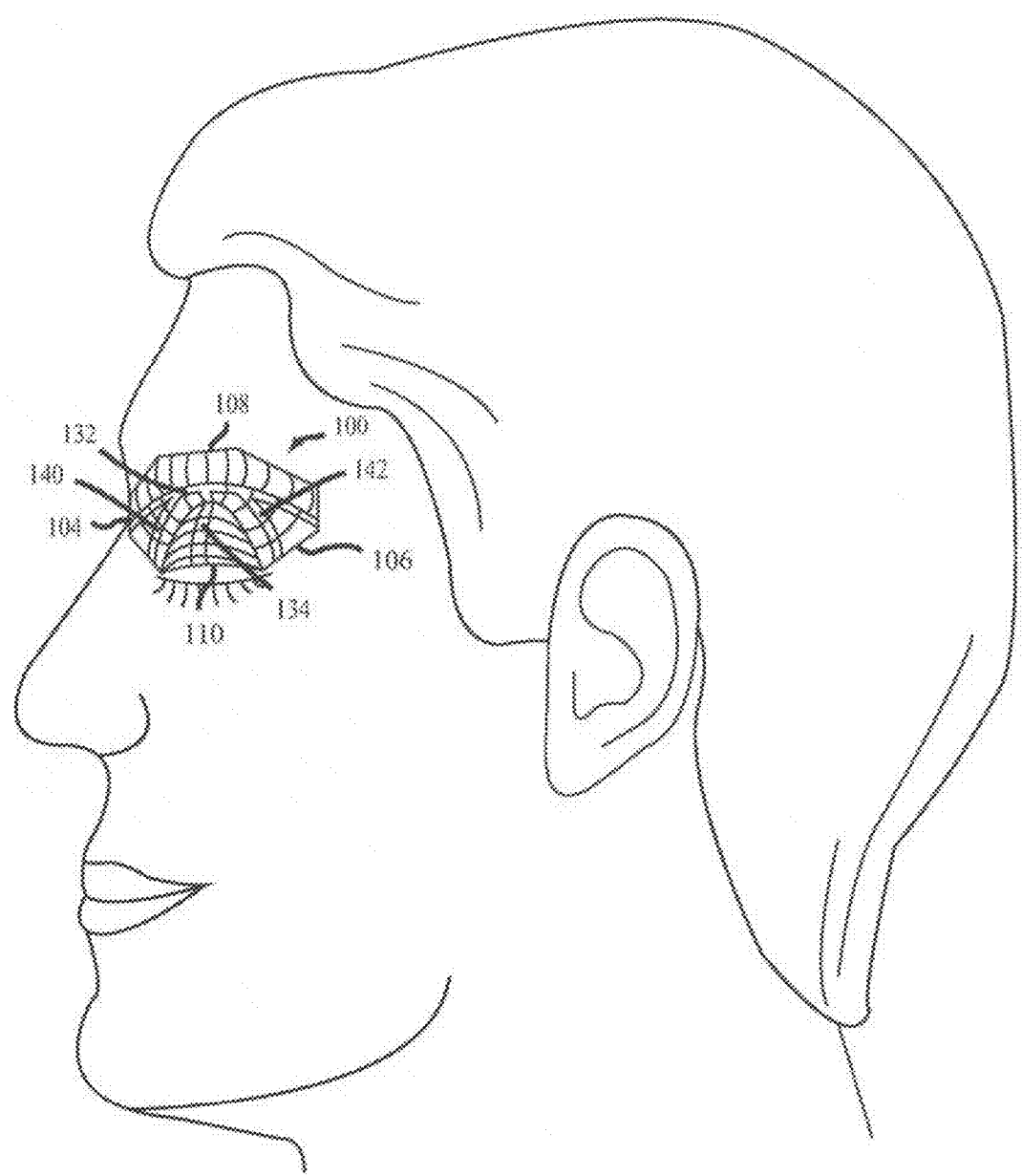
FIG. 17 is a side view of an embodiment of the improved eyelid support shown in FIG. 14, applied to an upper eyelid and brow of a user.
Figure 18:
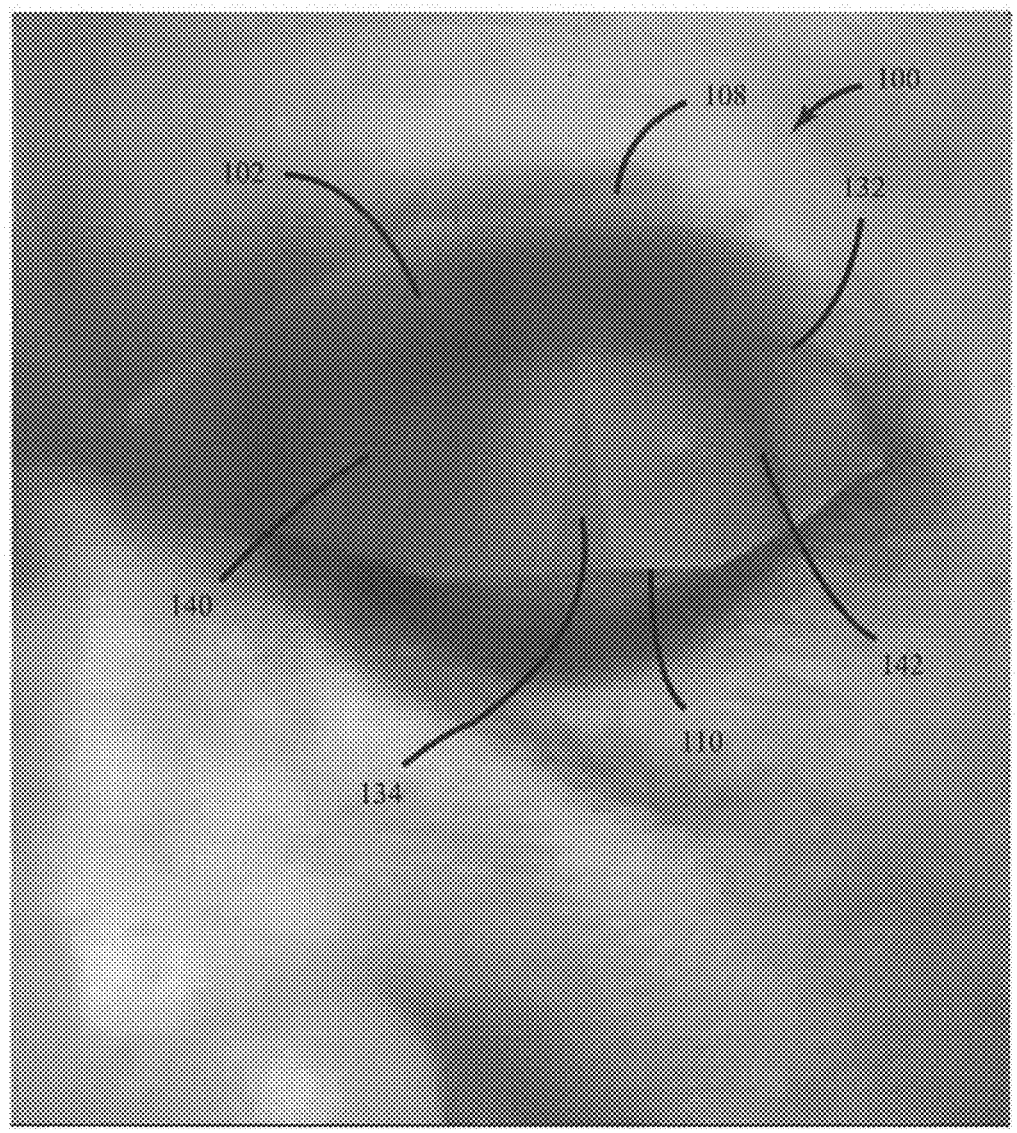
FIG. 18 is a close up front view photograph of the embodiment of the improved eyelid support shown in FIG. 14, applied to an upper eyelid and brow of a user.
Figure 19:
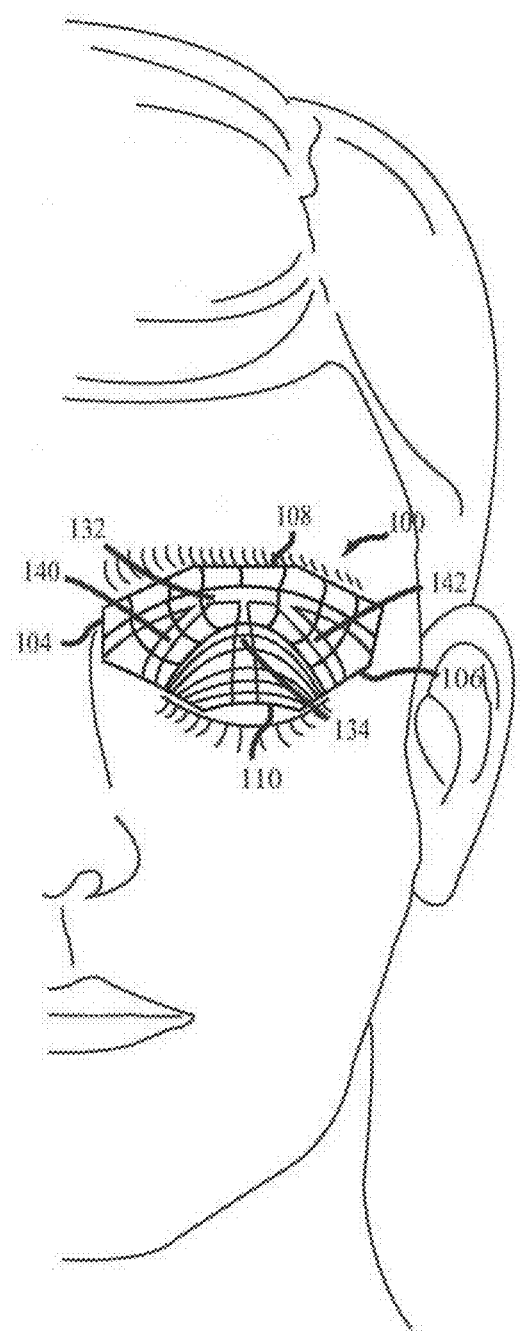
FIG. 19 is a front view of the embodiment of the improved eyelid support shown in FIG. 14, applied to an upper eyelid and brow of a user.

With reference to FIG. 15, in any embodiments disclosed herein, the support can have an overall width W of approximately 2⅝ inches, or from approximately 2 inches or less to approximately 3 inches or more, or to and from any values within this range. Additionally, any embodiments of the support can have an overall height H of approximately 1 inch, or from approximately 0.75 inch or less to approximately 1.5 inches or more, or to and from any values within this range. The width of the support along the bottom edge (designated by Wb in FIG. 15) in any embodiments can approximately 1 inch, or from approximately 0.75 inch or less to approximately 1.5 inches or more, or to and from any values within this range. The height of the support along the side edge (designated by Hs in FIG. 15) in any embodiments can approximately 0.375 inch, or from approximately 0.25 inch or less to approximately 0.5 inch or more, or to and from any values within this range. The length or width of the support along the chamfered or angled edge (designated by Wa in FIG. 15) in any embodiments can approximately 0.875 inch, or from approximately 0.75 inch or less to approximately 1.25 inches or more, or to and from any values within this range. In any embodiments, the thickness of the support can be approximately 0.011 inch, or from approximately 0.01 inch or less to approximately 0.05 inch or more, or to and from any values within this range.

FIG. 15 is a top view of another embodiment of an eyelid support 100. The embodiment of the eyelid support 100 can have any of the same features, materials, sizes, application methods or details, packaging details, or other details of any of the other embodiments disclosed herein, in combination with or in place of any of the features, materials, sizes, application methods or details, packaging details, or other details disclosed below with respect to the embodiment of the eyelid support 100. Similarly, any of the other embodiments disclosed herein can have any of the features, materials, sizes, application methods or details, packaging details, or other details of the embodiment of the eyelid support 100 in combination with or in place of any of the features, materials, sizes, application methods or details, packaging details, or other details disclosed for the respective embodiments. Any of the embodiments disclosed herein can, therefore, have any combination of any of the features, materials, sizes, or other details of the other embodiments disclosed herein.

As shown, the eyelid support 100 can have a main body 102 having a first lateral edge 104 that support can be inserted into or adjacent to an eye socket medial canthus of a user's face. A second lateral edge 106, or distal edge, of the eyelid support 100 can be opposite the medial edge 104. The eyelid support 100 can also define a superior edge 108 and an inferior edge 110. In any embodiments, the eyelid support 100 can be applied to support a user's eyelid in a closed position by applying the main body 102 of the support against a user's eyelid such that the inferior edge 110 of the eyelid support 100 is positioned just above the user's eyelashes L on the user's upper eyelid. The user can then gently press or conform the main body of the support 100 to the skin covering the user's eyeball, the eye socket above the eyeball, to the brow under the eyebrow (preferably, but not required, to be under the brow).

In any embodiments, the eyelid support can have an outside (or first) surface 120 and an inside (or second) surface 122 (not shown). The second surface 122 can be covered with a medically suitable adhesive such that, when a user applies the second surface 122 of the support 100 against the surface of the user's skin, the adhesive can be configured to create a removable but secure bond of the support to the user's sensitive skin, and can be configured to leave little to no residue upon removal of the support. Any suitable adhesive compatible with use with a person's skin can be applied to the second surface. Ideally, though not required, the entire second surface can be covered with adhesive.

Additionally, in any embodiments, the support 100 can have a plurality of higher flexibility flex zones 130 formed in the main body 102 of the eyelid support. The flex zones 130 can be configured to promote greater flexibility (i.e., less stiffness) and a greater propensity for folding or bending in the flex zones 130 portions of the main body 102. In any embodiments, the flex zones 130 can comprise preformed creases, folds, perforations, indentations, thinned material, higher flexibility material, and/or other similar features or materials or combinations of the foregoing. For example and without limitation, the flex zones 130 can have a thinner material thickness than the adjacent portions of the support 100 to promote greater bendability and flexibility in the flex zones 130 and, hence, greater conformability of the support 100 to the user's anatomy.

In any embodiments, one or more of the flex zones can be sized, shaped, and positioned to align generally with the locations of the support that correspond with changes in curvature of the support—for example, where the curvature of the support changes from concave to convex, or convex to concave. In any embodiments, one or more of the flex zones can be sized, shaped, and positioned to align generally with the locations of the user's anatomy having the sharpest curves—for example, along the inside edge of the user's eye socket, on the under brow portion of the user's face, and other locations where the curvature is the sharpest.

With reference to FIG. 15, the main body can have a first flex zone 132 (also referred to as a lateral flex zone) extending generally laterally across the main body 102 of the support 100. In any embodiments, the first flex zone 132 can be straight, curved (in the illustrated embodiment), or any desired shape. In some embodiments, first flex zone 132 can be curved to approximately match the curvature of an upper portion of an eye socket of a user to promote greater flexibility in the support in the region of the eye socket.

Additionally, any embodiments can also have a second flex zone 134 (also referred to as a medial flex zone) extending in an vertical direction generally in the middle of the support 100. The second flex zone 134 can increase the flexibility of the support 100 in a middle portion of the support 100 that approximately aligns with a middle portion of a user's eyelid, in a vertical direction when the support 100 is an upright position. An upper portion of the second flex zone 134 can join or abut the first flex zone 132.

Any embodiments of the support 100 can also have third and fourth flex zones 140, 142 that can be positioned generally to align with the lateral edges of the user's eyeball, or the edges of the eyelid aligned with the edges of the user's eyeball. The third and fourth flex zones 140, 142 can be positioned where the curvature of the support changes from convex (see convex region 164 in FIG. 18) to the concave region 162 to improve the flexibility and conformability of the support to the user's anatomy in those regions.

Figure 20:
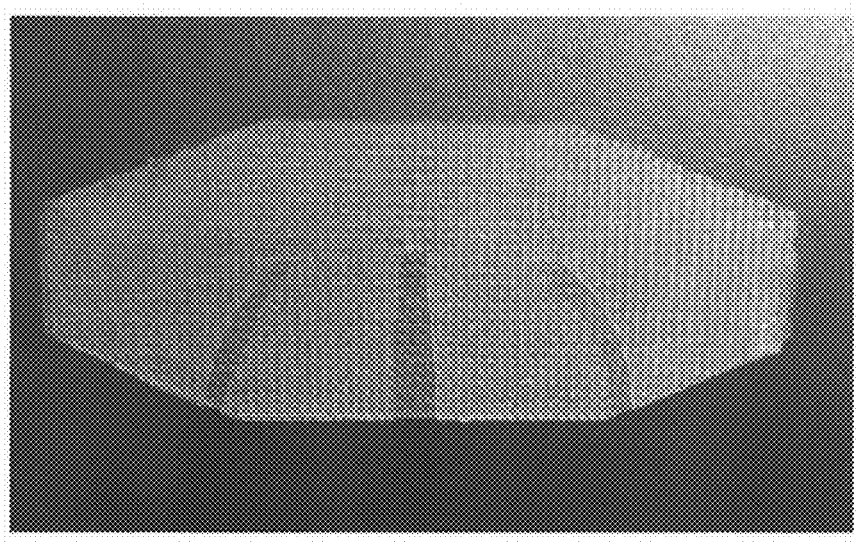
FIG. 20 is a top view photograph of another embodiment of an improved eyelid support.
Figure 21:
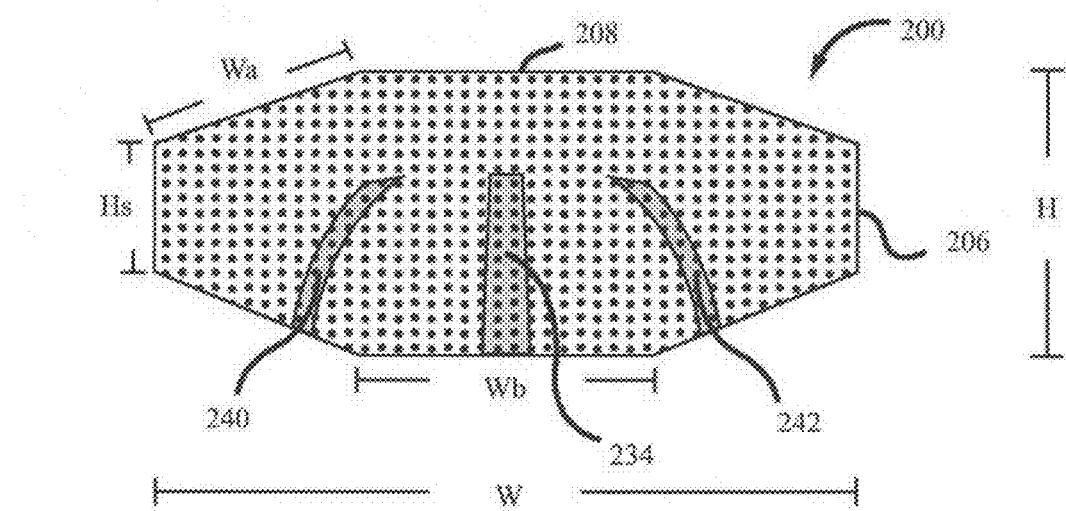
FIG. 21 is a top view of the embodiment of the improved eyelid support shown in FIG. 20, with exemplifying, nonlimiting measurements.
Figure 22:
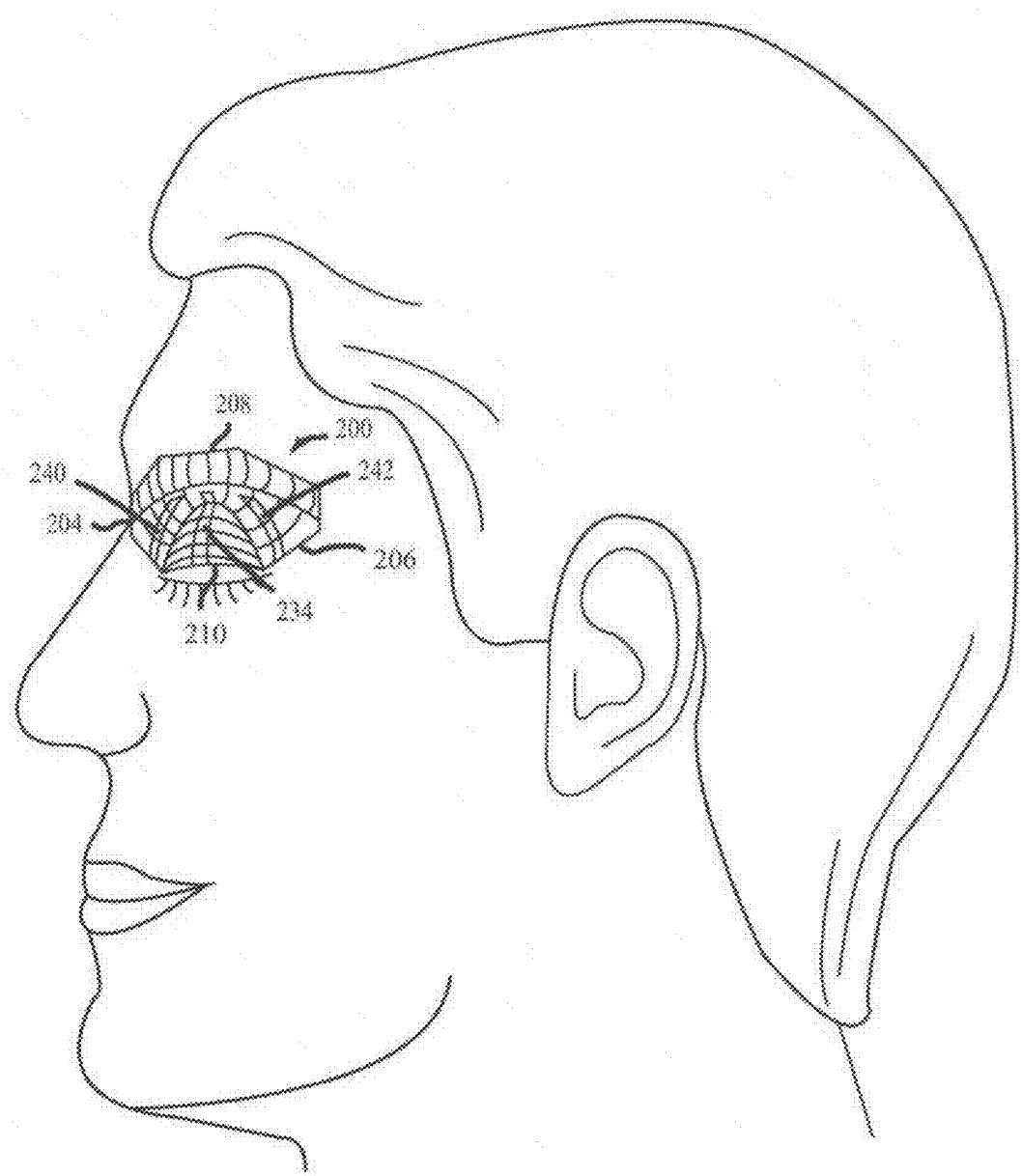
FIG. 22 is a side view of the embodiment of the improved eyelid support shown in FIG. 20, applied to an upper eyelid and brow of a user.
Figure 23:
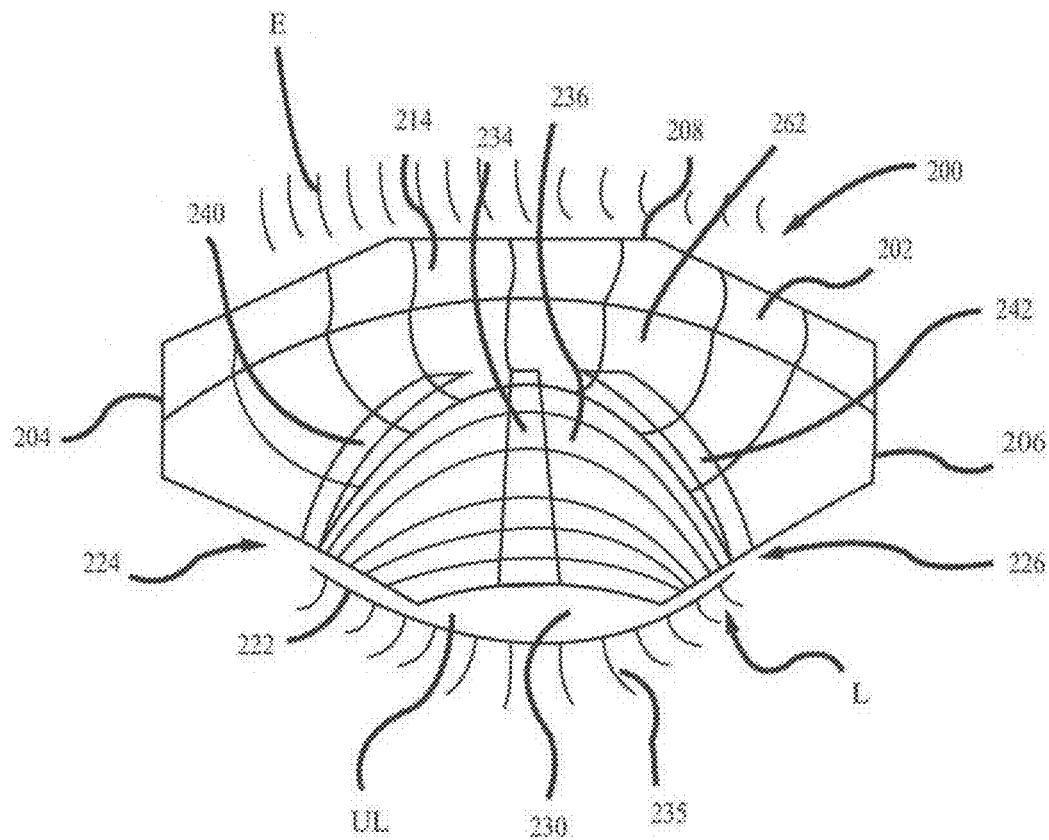
FIG. 23 is an enlarged view of the embodiment of the improved eyelid support shown in FIG. 20, applied to an upper eyelid and brow of a user.

FIG. 20 is a top view of another embodiment of an eyelid support 200. The embodiment of the eyelid support 200 can have any of the same features, materials, sizes, application methods or details, packaging details, or other details of any of the other embodiments disclosed herein, in combination with or in place of any of the features, materials, sizes, application methods or details, packaging details, or other details disclosed below with respect to the embodiment of the eyelid support 200. Similarly, any of the other embodiments disclosed herein can have any of the features, materials, sizes, application methods or details, packaging details, or other details of the embodiment of the eyelid support 200 in combination with or in place of any of the features, materials, sizes, application methods or details, packaging details, or other details disclosed for the respective embodiments. Any of the embodiments disclosed herein can, therefore, have any combination of any of the features, materials, sizes, or other details of the other embodiments disclosed herein.

As shown, the eyelid support 200 can have a main body 202 having a first lateral edge 204 that support can be inserted into or adjacent to an eye socket medial canthus of a user's face. A second lateral edge 206, or distal edge, of the eyelid support 200 can be opposite the medial edge 204. The eyelid support 200 can also define a superior edge 208 and an inferior edge 210. In any embodiments, the eyelid support 200 can be applied to support a user's eyelid in a closed position by applying the main body 202 of the support against a user's eyelid such that the inferior edge 210 of the eyelid support 200 is positioned just above the user's eyelashes L on the user's upper eyelid. The user can then gently press or conform the main body of the support 200 to the skin covering the user's eyeball, the eye socket above the eyeball, to the brow under the eyebrow (preferably, but not required, to be under the brow).

In any embodiments, the eyelid support can have an outside (or first) surface 220 and an inside (or second) surface 222 (not shown). The second surface 222 can be covered with a medically suitable adhesive such that, when a user applies the second surface 222 of the support 200 against the surface of the user's skin, the adhesive can be configured to create a removable but secure bond of the support to the user's sensitive skin, and can be configured to leave little to no residue upon removal of the support. Any suitable adhesive compatible with use with a person's skin can be applied to the second surface. Ideally, though not required, the entire second surface can be covered with adhesive.

Additionally, in any embodiments, the support 200 can have a plurality of higher flexibility flex zones 230 formed in the main body 202 of the eyelid support. The flex zones 230 can be configured to promote greater flexibility (i.e., less stiffness) and a greater propensity for folding or bending in the flex zones 230 portions of the main body 202. In any embodiments, the flex zones 230 can comprise preformed creases, folds, perforations, indentations, thinned material, higher flexibility material, and/or other similar features or materials or combinations of the foregoing. For example and without limitation, the flex zones 230 can have a thinner material thickness than the adjacent portions of the support 200 to promote greater bendability and flexibility in the flex zones 230 and, hence, greater conformability of the support 200 to the user's anatomy.

In any embodiments, one or more of the flex zones can be sized, shaped, and positioned to align generally with the locations of the support that correspond with changes in curvature of the support—for example, where the curvature of the support changes from concave to convex, or convex to concave. In any embodiments, one or more of the flex zones can be sized, shaped, and positioned to align generally with the locations of the user's anatomy having the sharpest curves—for example, along the inside edge of the user's eye socket, on the under brow portion of the user's face, and other locations where the curvature is the sharpest.

Figure 24:
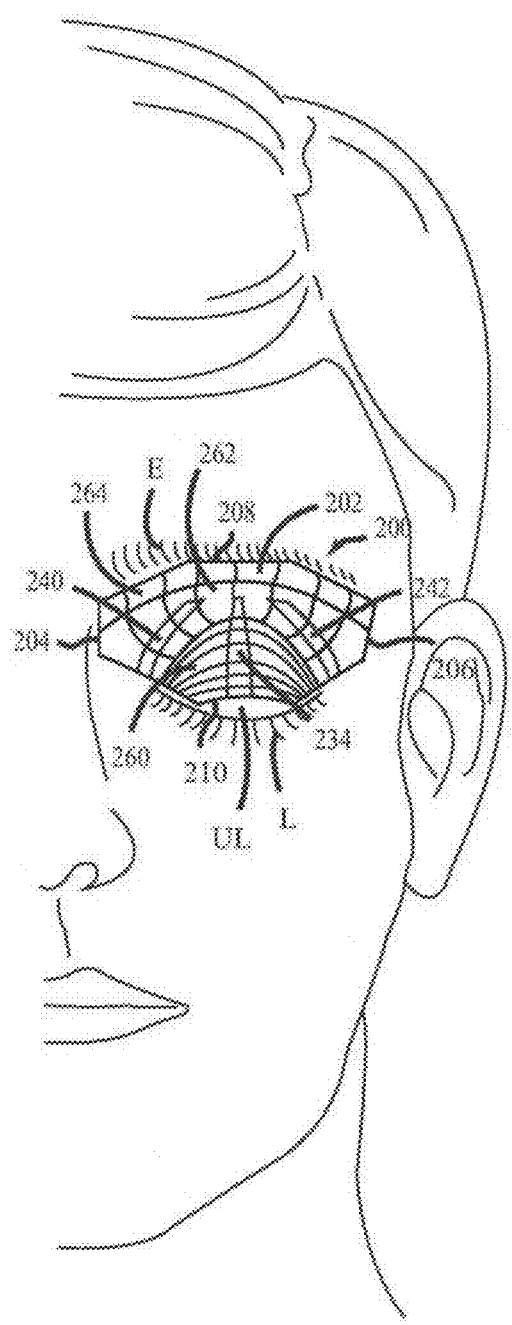
FIG. 24 is a front view of the embodiment of the improved eyelid support shown in FIG. 20.

With reference to FIG. 24, the main body can have a first flex zone 234 (also referred to as a medial flex zone) extending in an vertical direction generally in the middle of the support 200. The first flex zone 234 can increase the flexibility of the support 200 in a middle portion of the support 200 that approximately aligns with a middle portion of a user's eyelid, in a vertical direction when the support 200 is an upright position.

Any embodiments of the support 200 can also have second and third flex zones 240, 242. In some embodiments, the second and third flex zones 240, 242 can be positioned generally to align with the lateral edges of the user's eyeball, can be positioned to generally align with the edges of the user's eyelid so as to generally be aligned with the edges of the user's eyeball or lateral edges of the user's eye socket, or can be positioned to generally be adjacent to the edges of the eye socket. In any embodiments, the second and third flex zones 240, 242 can be positioned to generally align with or be adjacent to the portion of the main body 202 where the curvature of the support changes from convex (see convex region 264 in FIG. 24) to the concave region 262 to improve the flexibility and conformability of the support to the user's anatomy in those regions. The region 260 can be convex in both the lateral direction and in the vertical direction, when the support is applied to the skin covering the eye.

In any embodiments, the flex zone can have a width of approximately 0.1 inch, or from approximately 0.05 inch or less to approximately 0.2 inch or more, or from and to any values in this range. In some embodiments, the width of the flex zone can change along a length of the flex zone. For example and without limitation, the width of the second flex zone 234 can increase along a length of the second flex zone (when going from top to bottom). Any of the flex zones can have a tapering width or changing width along a length of the flex zones. Any flex zone (such as flex zone 234) can be tapered and can have a width of approximately 0.1 inches at a top portion of the flex zone and approximately 2 to 3 times that width at bottom of the flex zone.

Figure 25:
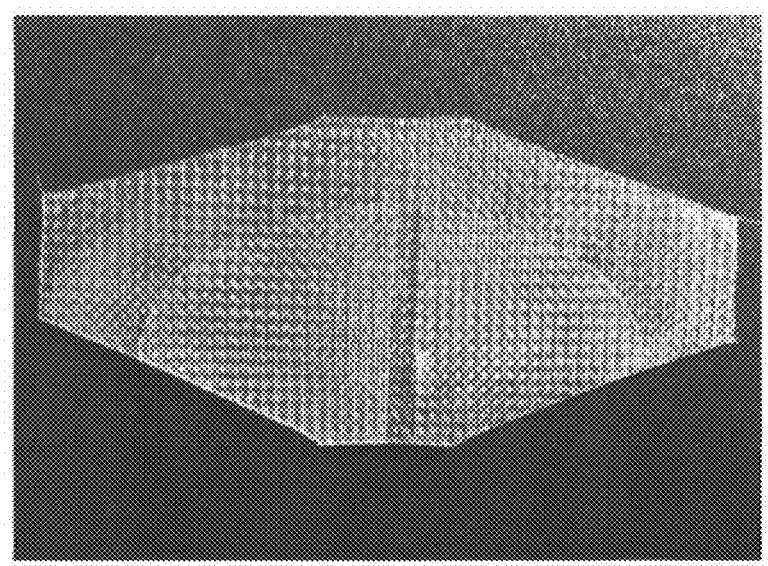
FIG. 25 is a photograph of a top view of another embodiment of an improved eyelid support.

FIG. 25 is a top view of another embodiment of an eyelid support 300. The embodiment of the eyelid support 300 can have any of the same features, materials, sizes, application methods or details, packaging details, or other details of any of the other embodiments disclosed herein, in combination with or in place of any of the features, materials, sizes, application methods or details, packaging details, or other details disclosed below with respect to the embodiment of the eyelid support 300. Similarly, any of the other embodiments disclosed herein can have any of the features, materials, sizes, application methods or details, packaging details, or other details of the embodiment of the eyelid support 300 in combination with or in place of any of the features, materials, sizes, application methods or details, packaging details, or other details disclosed for the respective embodiments. Any of the embodiments disclosed herein can, therefore, have any combination of any of the features, materials, sizes, or other details of the other embodiments disclosed herein.

Figure 26:
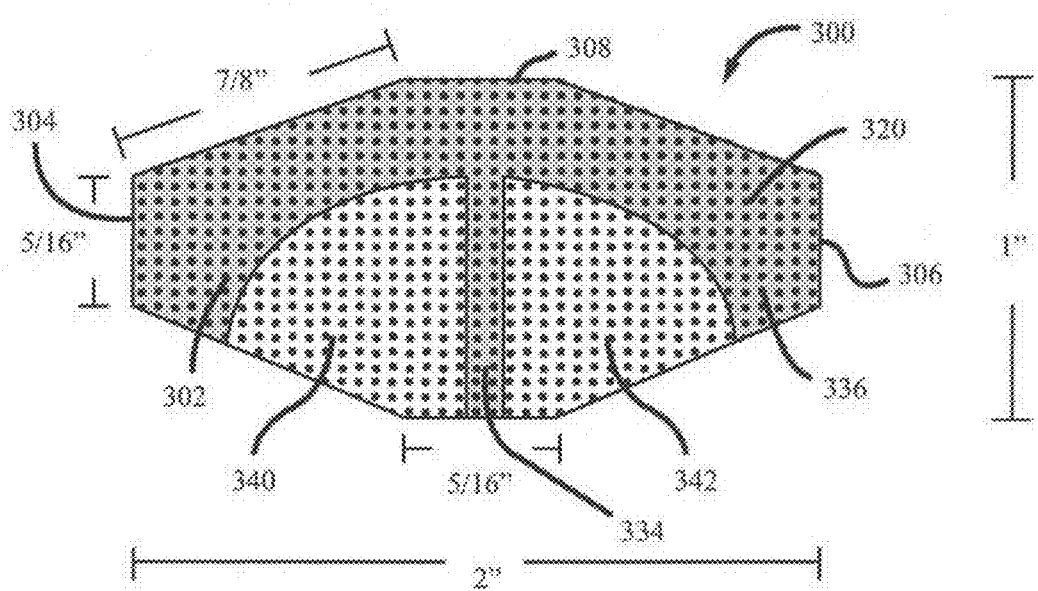
FIG. 26 is a top view of the embodiment of the improved eyelid support shown in FIG. 25, with exemplifying, non-limiting measurements.
Figure 27:
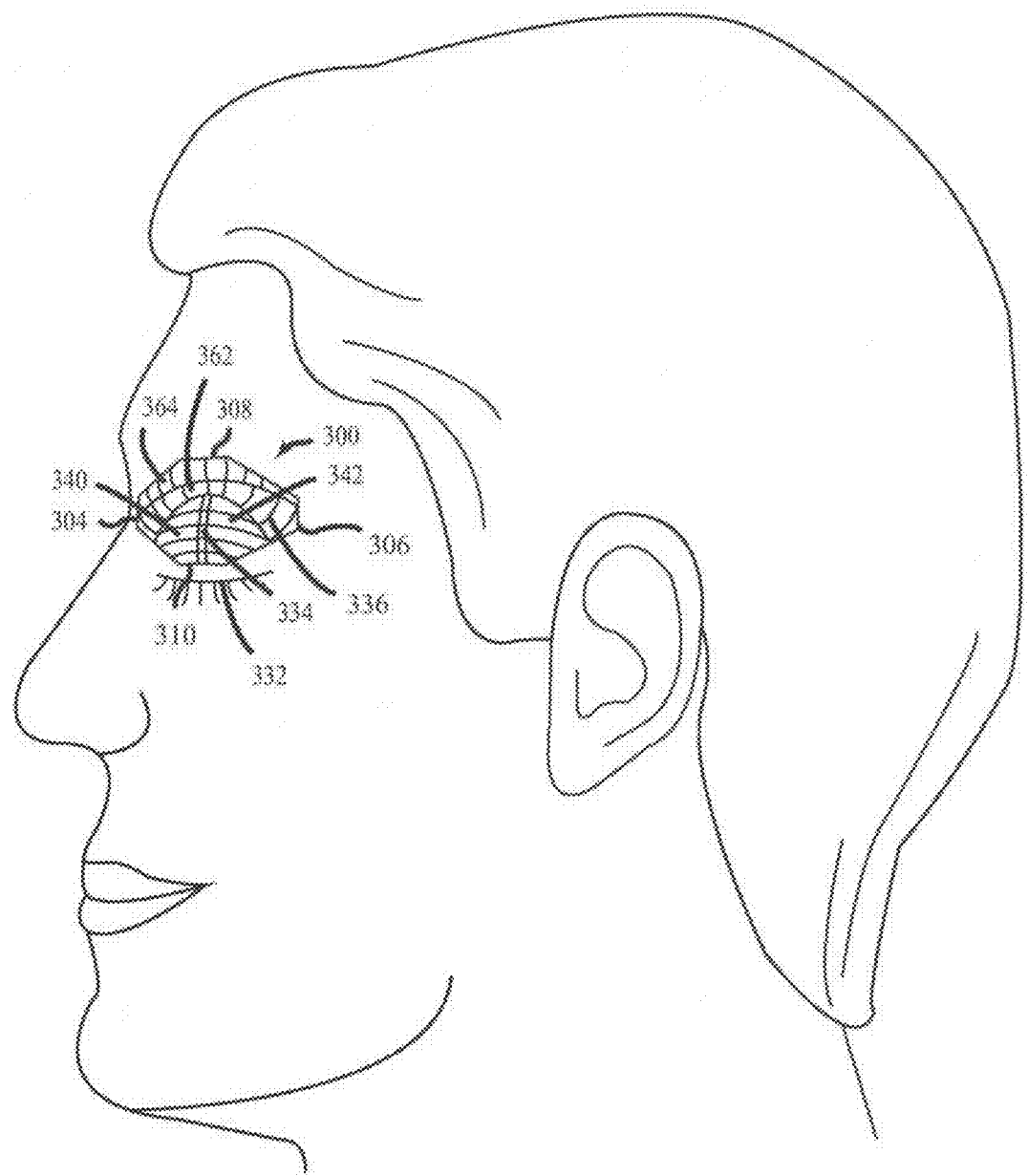
FIG. 27 is a side view of the embodiment of the improved eyelid support shown in FIG. 25, applied to an upper eyelid and brow of a user.
Figure 28:
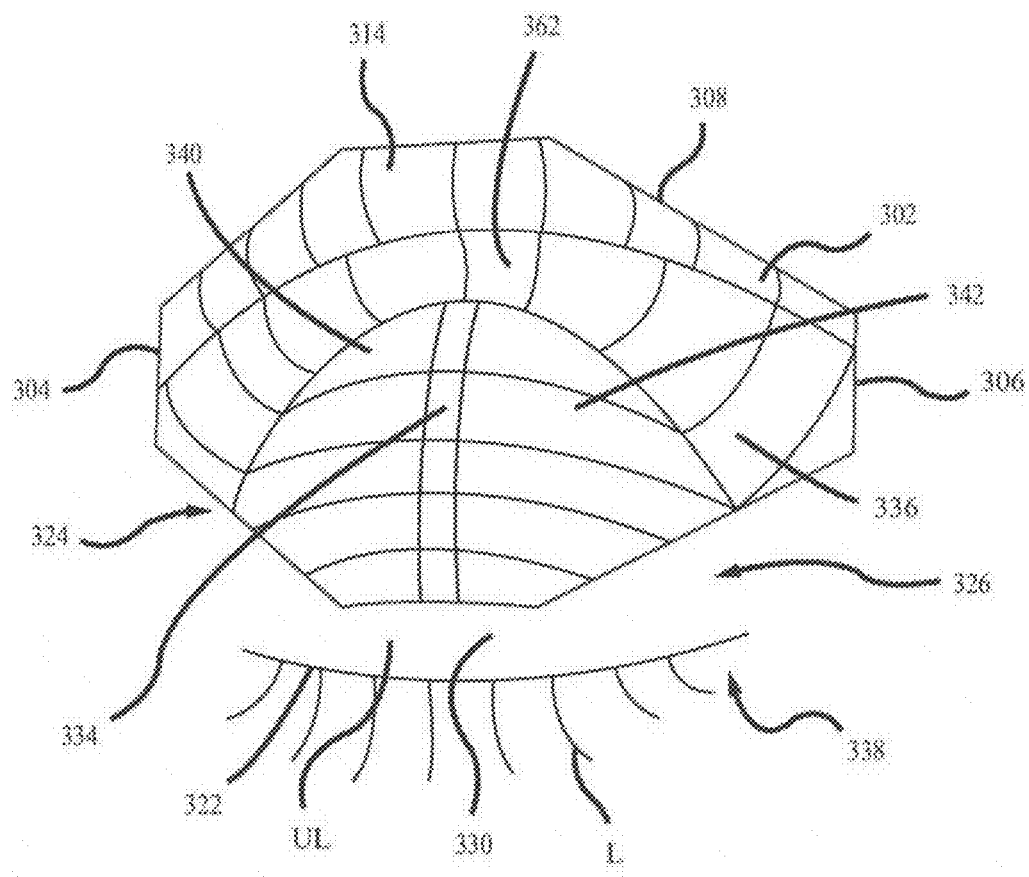
FIG. 28 is an enlarged view of the embodiment of the improved eyelid support shown in FIG. 25, applied to an upper eyelid and brow of a user.
Figure 29:
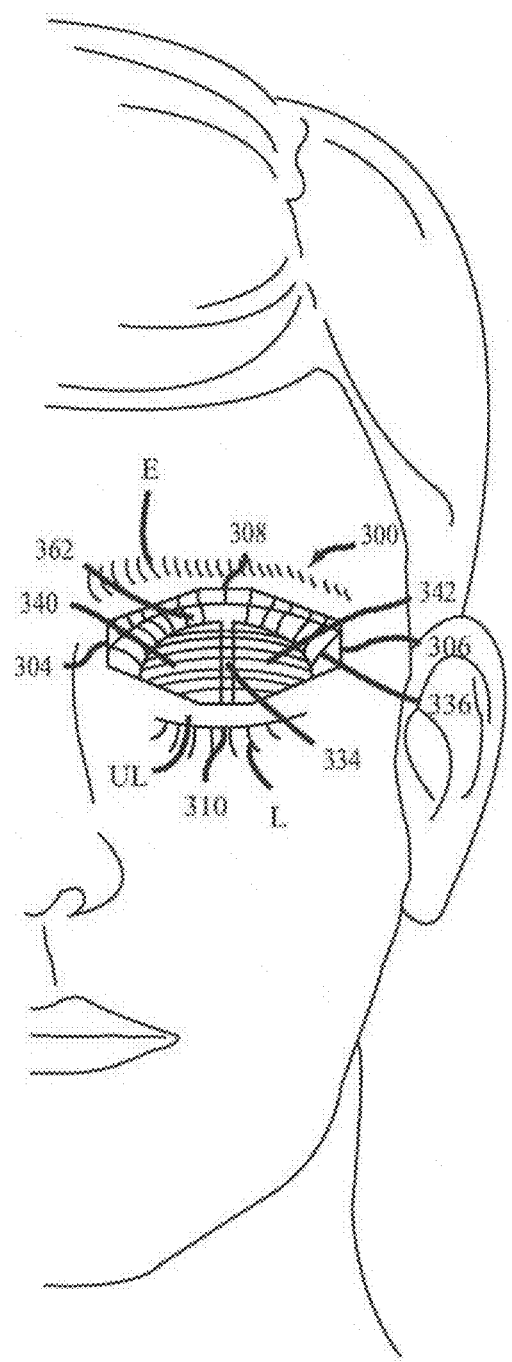
FIG. 29 is a front view of the embodiment of the improved eyelid support shown in FIG. 25.

With reference to FIG. 26, the eyelid support 300 can have a main body 302 having a first lateral edge 304 that can be inserted into or adjacent to an eye socket medial canthus of a user's face. A second lateral edge (or distal edge) 306 of the eyelid support 300 can be opposite the medial edge 304. The eyelid support 300 can also define a superior edge 308 and an inferior edge 310. In any embodiments, the eyelid support 300 can be applied to support a user's eyelid in a closed position by applying the main body 302 of the support against a user's eyelid such that the inferior edge 310 of the eyelid support 300 is positioned just above the user's eyelashes L on the user's upper eyelid. The user can then gently press or conform the main body of the support 300 to the skin covering the user's eyeball, the eye socket above the eyeball, to the brow under the eyebrow (preferably, but not required, to be under the brow). As in any illustrations, the dots or circles shown on the support can be used to represent micropores or perforations in the material, though such features are not required.

In any embodiments, the eyelid support can have an outside (or first) surface 320 and an inside (or second) surface 322 (not shown). The second surface 322 can be covered with a medically suitable adhesive such that, when a user applies the second surface 322 of the support 300 against the surface of the user's skin, the adhesive can be configured to create a removable but secure bond of the support to the user's sensitive skin, and can be configured to leave little to no residue upon removal of the support. Any suitable adhesive biocompatible with use with a person's skin can be applied to the second surface. In some embodiments, though not required, the entire second surface can be covered with adhesive.

As in any embodiments disclosed herein, the support 300 can have a one or more of higher flexibility flex zones formed in the main body 302 of the eyelid support. For example and without limitation, the support 300 can have a first or central flex zone 334 positioned in a lateral center of the support, and extending in a vertical direction. Any embodiments of the support disclosed herein, including without limitation support 300, can also have a second flex zone or region 336 which can be shaped and positioned to align with or cover the portion of the user's anatomy that is above the upper eyelid and/or to the sides of the upper eyelid, thereby providing a region (i.e., the second region) that has improved conformability to the user's anatomy around the eyelid and eyeball, including the brow above the eye socket and skin laterally adjacent to the user's eyelid. In some embodiments, the second flex zone 336 can be curved to approximately match the curvature of an upper portion of an eye socket of a user to promote greater flexibility in the support in the region of the eye socket.

In some embodiments, the main body can have a thickness in the flex zones that is less than a thickness of the main body adjacent to the flex zones. In any embodiments disclosed herein, the thickness of the main body (such as main body 302) can be approximately 0.35 mm, while a thickness of the main body in the flex zones can be approximately 0.30 mm or less, or approximately 0.25 mm or less, or from approximately 0.30 mm to approximately 0.20 mm. The flex zones 330 can be configured to promote greater flexibility (i.e., less stiffness) and a greater propensity for folding or bending in the flex zones 330 portions of the main body 302 than in the adjacent portions or zones of the main body 302. In any embodiments, the flex zones 330 can comprise preformed creases, folds, perforations, indentations, thinned material, higher flexibility material, a boundary of a thicker material abutting a thinner material or portion, that will flex or bend on the boundary or in the flex zone around the length or radius of arc or flange, and/or other similar features or materials or combinations of the foregoing. This also permits the support to have stiffer regions in portions where greater stiffness can improve the performance of the support. For example and without limitation, the flex zones 330 can have a thinner material thickness than the adjacent portions of the support 300 to promote greater bendability and flexibility in the flex zones 330 and, hence, greater conformability of the support 300 to the user's anatomy.

In any embodiments, one or more of the flex zones can be sized, shaped, and positioned to align generally with the locations of the support that correspond with changes in curvature of the support when the support is in an operable position—for example, where the curvature of the support changes from concave to convex, or convex to concave, in the operable position. In any embodiments, one or more of the flex zones can be sized, shaped, and positioned to align generally with the locations of the user's anatomy having the sharpest curves—for example, along the inside edge of the user's eye socket, on the under brow portion of the user's face, and other locations where the curvature is the sharpest.

Additionally, any embodiments can also have a second flex zone 334 (also referred to as a medial flex zone) extending in an vertical direction generally in the middle of the support 100. The second flex zone 334 can increase the flexibility of the support 300 in a middle portion of the support 300 that approximately aligns with a middle portion of a user's eyelid, in a vertical direction when the support 300 is an upright position. An upper portion of the second flex zone 334 can join or abut the first flex zone 332.

As described, the main body can have a first flex zone 334 and second flex zone 336. The main body 302 can have a first stiffened portion or zone (also referred to as a region) 340 and a second stiffened portion or zone 342 that can be sized, positioned, and otherwise configured to cover all or a portion of the user's eyelid, thereby providing additional stiffness to maintain the eyelid in the closed position. The first and second stiffened portions 340, 342 can be separated or spaced apart by the first flex zone 334. However, in some embodiments, the first stiffened zone can have an approximately semicircular shape that approximately matches the shape of the user's upper eyelid, without a flex zone therein. The first and second stiffened portions 340, 342 can have a thickness that is greater than the thickness of the flex zones. In some embodiments, the first and second stiffened regions can have a thickness of approximately 0.35 mm, or more, or from approximately 0.30 mm to approximately 0.40 mm.

Additionally, in any embodiments, the flexibility of the flex zones can vary from one flex zone to the next. The flexibility of the flex zone can be influenced by the thickness of the material in the flex zone, the length of the flex zone, the width of the flex zone, and whether there are other features formed in the flex zone that can further increase the flexibility of the flex zone. In any embodiments, the stiffness of the support in one or more of the flex zones can be approximately half of the stiffness of the support in the main body in other regions (non-flex zone regions) of the main body of the support (i.e., the flex zone portions of the support can be twice as flexible as the non-flex zone portions of the support). Alternatively, in any embodiments, the stiffness of the support in one or more of the flex zones can be from approximately 20% to approximately 80%, or from approximately 40% to approximately 60%, of the stiffness of the support in the main body in other regions (non-flex zone regions or stiffened regions) of the main body of the support.

Any embodiments of the eyelid support disclosed herein can be packaged individually, like a bandage, or with multiple supports per package, which can make the support more economical and affordable, even for users in rural areas and third world countries. Eyelid supports of the present disclosure can also be used by the military for treating eye injuries during combat. Some embodiments of the support can be worn and discarded daily. Some embodiments can be worn also at night while sleeping, as in cases of chronic dry eye, lazy eye, and stroke cases.

Embodiments of the device are effective to heal scratches and defects on the eyes surface, also to aid in healing after Lasik and or eye surgeries, or other conditions or ailments in which a doctor recommends closed eye treatment or healing. The eyelid support 2 can also be used by the elderly and children, and is configured to be easily applied by a caregiver. Any embodiments of the support can be produced in any of a range of possible sizes, to accommodate user's having different sized anatomies, etc. Additionally, in any embodiments, the shape of the support can be modified and adapted to different shapes and forms of eyes, due to varying facial characteristics and ethnicities. Embodiments of the support relieve unnecessary suffering and promote safe and comfortable healing.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the Figures. Depending on the embodiment, certain of the steps described above may be removed, others may be added. Accordingly, the scope of the present disclosure is intended to be defined only by reference to the claims of the utility application. The accompanying claims and their equivalents are intended to eyelid support such forms or modifications as would fall within the scope and spirit of the protection. Furthermore, the features and attributes of the specific embodiments disclosed above may be combined in different ways to form additional embodiments, all of which fall within the scope of the present disclosure. Although the present disclosure provides certain embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims or claims that will be added in the future.

Accordingly, although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future. Finally, as used herein and unless otherwise stated, the term approximately is meant to represent a range of +/−10% of the stated value.

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

The invention claimed is:

1. A support device for holding a superior tarsus of an eye in a closed position, comprising:
   a main body having a first main surface, a second main surface, a first lateral edge, a second lateral edge, a top edge, and a bottom edge;
     adhesive coupled with the second main surface, the second main surface being positionable against a user's upper eyelid when the support device is in an operable position;
     a first flex zone formed in the main body of the support device, the flex zone having a bend stiffness that is lower than a bend stiffness of portions of the main body adjacent to the flex zone;
   wherein:
     the support device is sized and configured to be positioned above a user's upper eyelash and below a user's eyebrow;
     the support device is configured to be conformed against a skin surface of the user above the user's upper eyelid when the user's upper eyelid is in a close position;
     the support device is configured to hold the user's upper eyelid in a closed position; and
     the first flex zone if configured to improve the conformability of the support device to the user's anatomy.

2. The device of claim 1, wherein the first flex zone has a curved shape and extends between the first lateral edge and the second lateral edge.

3. The device of claim 1, wherein the first flex zone has a curved shape and is configured to align approximately with an upper edge of a user's eye socket.

4. The device of claim 1, wherein the first flex zone has a curved shape and is configured to be positioned just below a user's brow.

5. The device of claim 1, further comprising a second flex zone, extending in a vertical direction approximately along a lateral midline when the support device is in an operable position.

6. The device of claim 5, wherein the second flex zone has an increasing width that is greater at a bottom portion of the second flex zone than at an upper portion of the second flex zone.

7. The device of claim 1, wherein the main body has a thickness in the first flex zone that is at least approximately 20% less than a thickness of the main body in the non-flex zone portions of the main body of the support device adjacent to the first flex zone.

8. The device of claim 1, wherein the first flex zone has a width of approximately 0.1 inch.

9. The device of claim 1, wherein the bend stiffness of the main body in the first flex zone
   is at least approximately 20% less than a stiffness of the main body adjacent to the first flex zone.

10. The device of claim 1, wherein the main body is made from a vapor permeable material.

11. A support member for holding a user's upper eyelid in a closed position, comprising:
    a main body having a first main surface, a second main surface, a first lateral edge, a second lateral edge, a top edge, and a bottom edge;
    adhesive applied to the second main surface, the second main surface being the surface that is positionable against a user's upper eyelid when the support member is in an operable position;
    a first stiffened zone formed in the main body of the support member; and
    a first flex zone formed in the main body of the support member;
    wherein:
      the support member is configured to be conformed against a skin surface of the user above the user's upper eyelid when the user's upper eyelid is in a close position;
      the support member is sized and configured such that the bottom edge is positioned above the user's upper eyelash when the support member is in an operable position on the user;
      the support member is sized and configured such that the top edge is positioned on the user's brow when the support member is in an operable position on the user;
      the support member is configured to hold the user's upper eyelid in a closed position when the support member is in an operable position on the user; and
      the first stiffened zone has a thickness that is significantly greater than a thickness of the first flex zone;
      the first stiffened zone is sized and positioned on the main body to generally cover the user' supper eyelid when the support member is in an operable position on the user; and
      the first flex zone positioned above and to the sides of the first stiffened zone to increase the flexibility of the main body in the main body adjacent to the first stiffened zone.

12. The support member of claim 11, wherein the first stiffened zone is configured to not extend substantially above the user's upper eyelid when the support member is in an operable position on the user.

13. The support member of claim 11, where in the first flex zone is configured to cover the user's brow when the support member is in an operable position on the user.

14. The support member of claim 11, wherein the first stiffened zone has a semicircular shape that approximately matches the shape of the user's upper eyelid.

15. The support member of claim 11, further comprising a second flex zone, extending in a vertical direction and being positioned generally in a lateral middle portion of the support member when the support member is in an operable position.

16. The support member of claim 11, wherein the main body has a thickness in the first stiffened zone that is at least approximately 15% greater than a thickness in the first flex zone.

17. The support member of claim 11, wherein the main body is made from a vapor permeable material.

\* \* \* \* \*